United States Patent

Orchard et al.

(10) Patent No.: US 6,740,670 B2
(45) Date of Patent: May 25, 2004

(54) THIAZOLIDINE DERIVATIVES AND ITS USE AS ANTIFUNGAL AGENT

(75) Inventors: Michael Glen Orchard, Great Britain (GB); Judi Charlotte Neuss, Great Britain (GB)

(73) Assignee: Oxford Glycosciences (UK) Ltd., Abingdon (GB)

(*) Notice: Subject to any disclaimer, the term of this patent is extended or adjusted under 35 U.S.C. 154(b) by 0 days.

(21) Appl. No.: 10/371,979

(22) Filed: Feb. 21, 2003

(65) Prior Publication Data

US 2003/0216453 A1 Nov. 20, 2003

Related U.S. Application Data

(63) Continuation of application No. PCT/GB01/03860, filed on Aug. 30, 2001.

(30) Foreign Application Priority Data

Aug. 31, 2000 (GB) .............................................. 0021419

(51) Int. Cl.$^7$ ..................... A61K 31/425; C07D 277/04
(52) U.S. Cl. ....................................... 514/369; 548/183
(58) Field of Search ........................... 514/369; 548/183

(56) References Cited

U.S. PATENT DOCUMENTS 3,704,296 A 11/1972 Mousseron

FOREIGN PATENT DOCUMENTS

| EP | 0047109 A1 | 10/1982 |
|---|---|---|
| WO | WO 00/18747 | 4/2000 |

OTHER PUBLICATIONS

AN 1997–010295, Derwent Publications Ltd., SU 1417436A (Chem Pharmacy Inst.) Abstract, Apr. 27, 1996.
Search Report mailed Dec. 3, 2001 in International Application No. PCT/6B01/03860.

*Primary Examiner*—Deborah C. Lambkin
(74) *Attorney, Agent, or Firm*—Darby & Darby

(57) ABSTRACT

Compounds of formula (I) or salts thereof are provided wherein X is O or S, A and B are OR2 or Y—NR3R4 wherein when A is OR2. B is Y—NR3R4 and vice versa, or when one of A or B is OR2. then the other can be $CO_2R7$. Y is $CH_2$ or C=Q. Q is $(CH_2)_m$—CH(R1)—$(CH_2)_n$, R is OR6 or NHR7 and with the other definitions as set out in claim 1, a process for its preparation and its use in the prophylaxis or treatment of fungal infections.

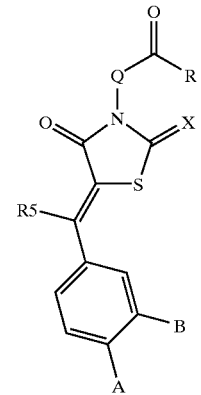

Formula I

9 Claims, No Drawings

THIAZOLIDINE DERIVATIVES AND ITS USE AS ANTIFUNGAL AGENT

CROSS REFERENCE TO RELATED APPLICATIONS

This is a Continuation of International Application No. PCT/GB01/03860 filed Aug. 30, 2001, which claims priority of United Kingdom Application No. 0021419.7, filed Aug. 31, 2000. The International Application was published in English on Mar. 21, 2002 as WO 02/22612 A1 under PCT Article 21(2).

The present invention relates to novel compounds, pharmaceutical compositions comprising novel compounds and novel compounds for use in medicine especially as antifungal agents. In addition, the invention provides compounds for the preparation of a medicament for use as an antifungal agent and methods of treating an individual susceptible to or suffering from an antifungal infection.

Fungal infections can affect animals including humans. These can include infections of the joints and skin. Some fungal infections occur as a result of opportunistic infection of a weakened or immune-suppressed individual. The incidence of life-threatening fungal infections has increased dramatically as the population of immunocompromised individuals (including cancer, organ transplant and AIDS patients) has increased. Present therapeutic options for the treatment of these infections are limited to two classes of compound: polyenes and azoles. The utility of polyenes is limited by nephrotoxicity and resistance is emerging to azoles. There is therefore a need for new anti-fungal compounds with novel mechanisms of action for use in treating or preventing such fungal infections.

WO94/29287 discloses arylidene-4-oxo-2-thioxo-3-thiazolidine carboxylic acids of the formula

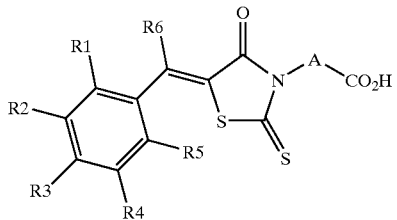

and their use in the treatment of atherosclerosis, arteriosclerosis and the late effects of diabetes.

WO00/18747 discloses rhodanine carboxylic acid derivatives of the formula

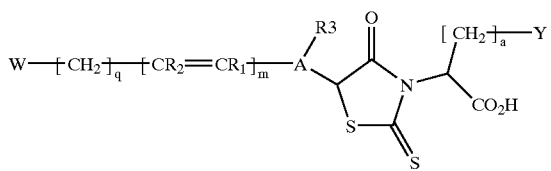

for the treatment and prevention of metabolic bone disorders.

We have now found that certain thiazolidine derivatives exhibit antifungal activity.

The first aspect of the present invention provides a compound of formula I or a salt thereof

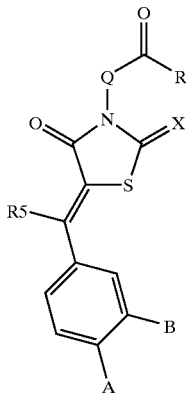

Formula I wherein X is O or S,

A and B are OR2 or Y—NR3R4
wherein when A is OR2, B is Y—NR3R4 and vice versa, or when one of A or B is OR2, then the other can be $CO_2R7$, Y is $CH_2$ or C=O, Q is $(CH_2)_m$—CH(R1)—$(CH_2)_n$, R is OR6 or NHR7, R1 is hydrogen, $C_1$–$C_6$ branched or straight chain optionally substituted with hydroxyl, $C_1$–$C_3$ alkylphenyl or phenyl, R2 is hydrogen, $C_1$–$C_{10}$ branched or straight chain alkyl or cycloalkyl, $C_1$–$C_{10}$ branched or straight chain alkenyl, $C_1$–$C_{10}$ branched or straight chain alkynyl, $(CH_2)_m$—$(CF_2)_n CF_3$, $(CH_2)_n$—CH(R10)—$(CH_2)_q$-aryl or $(CH2)_p$-aryl, where aryl is phenyl, pyridyl, thienyl or furyl;

wherein phenyl is optionally substituted by one or more substituents selected from F, Cl, Br, $CF_3$, $OCF_3$, OR6, $C_1$–$C_6$ branched or straight chain alkyl, COR, CN, $SO_2R8$, SONR8R9, and pyridyl, thienyl or furyl are optionally substituted by F, Cl, Br, $CF_3$, OR6 or C1–C6 branched or straight chain alkyl, R3 and R4 are independently hydrogen, $C_1$–$C_6$ branched or straight chain alkyl, C(=O)R6, —CH($CH_2$OCOR8)-aryl or CH(R8)—$(CH_2)_p$-aryl where aryl is phenyl, pyridyl, thienyl or furyl wherein phenyl is optionally substituted by one or more substituents selected from F, Cl, Br, $CF_3$, $OCF_3$, OR6, $C_1$–$C_6$ branched or straight chain alkyl, COR, CN, $SO_2R8$ or phenyl, R3 and R4 may be the same or different; taken together R3, R4 may form a 4–7 membered ring optionally incorporating an additional heteroatom, for example O, N or S wherein the ring may be optionally substituted at any position with $(CH_2)_p$-aryl where aryl is phenyl optionally substituted by one or more substituents selected from F, Cl, Br, $CF_3$, $OCF_3$, $C_1$–$C_6$ branched or straight chain alkyl, COR, CN, SO2R8 or phenyl, R5 is hydrogen, $C_1$–$C_6$ branched or straight chain alkyl or phenyl optionally substituted by one or more substituents selected from F, Cl, Br, $CF_3$, $OCF_3$, OR6, $C_1$–$C_6$ branched or straight chain alkyl, COR, CN or $SO_2R8$, R6 and R7 are independently hydrogen or $C_1$–$C_{10}$ branched or straight chain alkyl or $(CH_2)_p$-phenyl R8 is hydrogen or $C_1$–$C_3$ alkyl.

R9 is $C_1$–$C_6$ branched or straight chain alkyl or phenyl,

R10 is hydrogen, $C_1$–$C_{10}$ branched or straight chain alkyl, $(CH_2)_p$-Aryl where aryl is phenyl optionally substituted by one or more substituents selected from F, Cl, Br, $CF_3$, $OCF_3$, $C_1$–$C_6$ branched or straight chain alkyl, COR, CN, $SO_2R8$, and m, n and p are integers wherein m=0–3; n=0–2; p=0–3.

In a preferred embodiment compounds of formula I are provided in which:

X is O or S;

A and B are OR2 or Y—NR3R4

Wherein when A is OR2, B is Y—NR3R4 and vice versa, or when one of A or B is OR2, then the other can be $CO_2R6$;

Y is $CH_2$ or C=O;

Q is CH(R1);

R is OH;

R1 is hydrogen, $C_1$–$C_6$ alkyl or $C_1$–$C_3$ alkylphenyl;

R2 is hydrogen, $C_1$–$C_{10}$ branched or straight chain alkyl, $(CH_2)_p$-phenyl, wherein phenyl is optionally substituted by one or more substituents selected from F and $CF_3$;

R3 and R4 are independently hydrogen, $C_1$–$C_6$ branched or straight chain alkyl, $(CH_2)_p$-phenyl, C(=O)$C_1$–$C_{10}$ branched or straight chain alkyl, —CH(CR8)-phenyl —CH($CH_2$OCOR8)-phenyl, or R3 and R4 together form a morpholino, piperidinyl or piperazinyl group optionally substituted with $(CH_2)_p$-phenyl; and R5 is hydrogen; and wherein p is an integer=0–3.

Preferred compounds of the invention include;

5-[[[3-(N-methyl-N-phenylamino)carbonyl-4-(phenylmethoxy)]-phenyl]methylene]-4-oxo-2-thioxo-3-thiazolidineacetic acid;

5-[[[3-(N,N-Dibenzylamino)carbonyl-4-(phenylmethoxy)]-phenyl]methylene]-4-oxo-2-thioxo-3-thiazolidineacetic acid;

5-[[[3-(N,N-Dipentylamino)carbonyl-4-(phenylmethoxy)]-phenyl]methylene]-4-oxo-2-thioxo-3-thiazolidineacetic acid;

5-[[[3-((S)-N-Benzyl-N-alpha-methylbenzylamino)carbonyl-4-(phenyl-methoxy)]-phenyl]methylene]-4-oxo-2-thioxo-3-thiazolidineacetic acid;

5-[[[3-(N,N-Dibutylamino)carbonyl-4-(phenylmethoxy)]-phenyl]methylene]-4-oxo-2-thioxo-3-thiazolidineacetic acid;

5-[[[3-(N-Benzyl-N-butylamino)carbonyl-4-(phenylmethoxy)]-phenyl]methylene]-4-oxo-2-thioxo-3-thiazolidineacetic acid;

5-[[[3-((R)-N-alpha-methylbenzylamino)carbonyl-4-(phenylmethoxy)]-phenyl]methylene]-4-oxo-2-thioxo-3-thiazolidineacetic acid;

5-[[[3-((S)-N-methyl-N-alpha-methylbenzylamino)carbonyl-4-(phenylmethoxy)]-phenyl]methylene]-4-oxo-2-thioxo-3-thiazolidineacetic acid;

5-[[[3-(Dipentylamino)carbonyl-4-methoxy]phenyl]methylene]-4-oxo-2-thioxo-3-thiazolidineacetic acid;

5-[[[3-((S)-N-Benzyl-N-alpha-methylbenzylamino)carbonyl-4-methoxy]-phenyl]methylene]-4-oxo-2-thioxo-3-thiazolidineacetic acid;

5-[[[3-(N,N-Dipentylamino)carbonyl-4-[(2,4-difluorophenyl)-methoxy]]phenyl]methylene]-4-oxo-2-thioxo-3-thiazolidineacetic acid;

5-[[[3-(N,N-Dipentylamino)carbonyl-4-(trifluorophenyl)-methoxy]phenyl]methylene]-4-oxo-2-thioxo-3-thiazolidineacetic acid;

5-[[3-[(Dibenzylamino)methyl]-4-(phenylmethoxy)phenyl]methylene]-4-oxo-2-thioxo-3-thiazolidineacetic acid;

5-[[3-[(Dipentylamino)methyl]-4-(phenylmethoxy)phenyl]methylene]-4-oxo-2-thioxo-3-thiazolidineacetic acid;

(R)-5-[[[3-(N-α-(Acetoxymethyl)benzyl-N-benzylamino)carbonyl-4-(phenylmethoxy)]-phenyl]methylene]-4-oxo-2-thioxo-3-thiazolidineacetic acid;

5-[[[3-(N,N-Dipentylamino)carbonyl-4-(2-phenylethoxy)]-phenyl]methylene]-4-oxo-2-thioxo-3-thiazolidineacetic acid;

5-[[4-(2-Phenylethoxy)-3-[(N-phenyl-N-2-n-propyl-n-pentylcarbonyl)aminomethyl]-phenyl]methylene]-4-oxo-2-thioxo-3-thiazolidineacetic acid.

The invention also extends to prodrugs of the aforementioned compounds. A prodrug is commonly described as an inactive or protected derivative of an active ingredient or a drug which is converted to the active ingredient or drug in the body. In addition, the invention extends to active derivatives of the aforementioned compounds.

Where a compound of the invention contains one or more chiral centres, the compound can be provided as a single isomer (R or S) or a mixture of isomers for example, a racemic mixture. Where a substituent contains an alkene moiety, the alkene can be present as a cis or trans isomer or a mixture thereof.

Examples of pharmaceutically acceptable salts of the above compounds include those derived from inorganic and organic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases that are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl)aminomethane; and the like. Where appropriate salts can also be formed with organic acids such as methanesulphonic acid, benzenesulphonic acid and p-toluenesulphonic acid, or mineral acids such as hydrochloric and sulphuric acid and the like, giving methanesulphonate, benzenesulphonate, p-toluenesulphonate, hydrochloride and sulphate salts, and the like, respectively.

Salts may be prepared in a conventional manner using methods well known in the art.

The second aspect of the invention relates to a pharmaceutical composition of a compound of the first aspect of the invention. The pharmaceutical formulation will provide a compound of the first aspect of the invention and, optionally, a pharmaceutically acceptable carrier.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions).

Suitable excipients for tablets or hard gelatine capsules include lactose, maize starch or derivatives thereof, stearic acid or salts thereof.

Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions, oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research*, 3 (6):318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulisers or insufflators.

Pharmaceutical compositions-adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilised) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substance of the present invention can vary between wide limits, depending upon the disease or disorder to be treated, the age and condition of the individual to be treated, etc. and a physician will ultimately determine appropriate dosages to be used. This dosage may be repeated as often as appropriate. If side effects develop the amount and/or frequency of the dosage can be reduced, in accordance with normal clinical practice. The likely dosage of the substance is an effective dosage of 0.1–750 milligrams/kg/day, preferably 0.1–10 milligrams/kg/day.

It should be understood that in addition to the ingredients particularly mentioned above, the formulations may also include other agents conventional in the art having regard to the type of formulation in question, for example those suitable for oral administration may contain flavouring agents.

All preferred features of the first aspect of the invention also apply to the second aspect.

A third aspect of the invention provides a method for the manufacture of the compounds of the first aspect of the invention.

The compounds of this invention can be prepared by condensation of rhodanine-3-acetic acid or an analogue or derivative thereof with the appropriate substituted benzaldehyde derivative under general acid-base catalysis conditions using typical reagents for such a process, e.g. sodium acetate in acetic acid or ammonium acetate in a suitable solvent such as toluene, usually with the application of heat and preferably at the reflux temperature of the solvent (Scheme 1).

Scheme 1

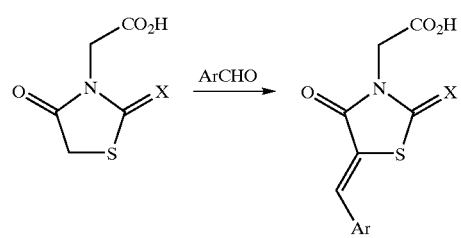

Rhodanine-3-acetic acid and the benzaldehyde derivatives are either commercially available, can readily be prepared by a skilled person or are synthesised by the methods outlined in the examples.

A compound of general formula (I) may be transformed into another compound of general formula (I) using methods well known to those skilled in the art. If protection of a particular functional group is required, this can be achieved using protecting groups and conditions known in the art. The protecting groups may be removed at any stage in the synthesis of the compounds of formula I or may be present on the final compound of formula I.

The third aspect of the invention also provides novel intermediate compounds in the formation of compounds of formula I.

All preferred features of the first and second aspects of the invention also apply to the third aspect.

The fourth aspect of the invention provides a compound of the first aspect of the invention for use in medicine.

In one feature of the fourth aspect of the invention provides a compound of formula I for use as an anti-fungal agent.

For the purposes of this invention, an anti-fungal agent is a compound or composition which alleviates or reduces the symptoms of a fungal infection or an agent which causes harm to fungus allowing the destruction of a fungus either by the agent, a second agent or the hosts natural defenses (e.g. the immune system). The anti-fungal agent can be used in the curative or prophylactic treatment of fungal infections.

The fourth aspect provides a compound which can be administered to humans or animals especially domestic animals such as dogs, cats, horses etc.

The compound of the first aspect of the invention can be used to treat topical infections caused by species of fungus including Candida, Trichophyton, Microsporum and Epidermophyton or in mucosal infections caused by species of fungus including *Candida albicans* (e.g. thrush and vaginal candidiasis). They can also be used in the treatment of infections caused by, for example, species of Candida (e.g. *Candida albicans*), *Cryptococcus neoformans, Aspergillus flavus, Aspergillus fumigatus*, Coccidioides, Paracoccidioides, Histoplasma or Blastomyces.

The cell wall of Candida and other pathogenic fungal species is essential for the survival of the organism. Defects in the wall structure will result in cell swelling and ultimately death through rupture. The unique nature of the wall has made its synthesis and re-modelling a focus for the development of novel anti-fungal agents. The wall consists of three major components: complex $\beta$1-3 and $\beta$1-6 linked glucan chains, chitin and cell wall mannoproteins. The $\beta$-glucans represent 50–60% of the cell wall mass, forming a rigid skeletal structure responsible for shape and physical strength. The chitin is only a minor component (>3%), but forms a structure to which the $\beta$-glucan is linked and is essential for bud scar formation during cell division. There are a number of agents that are being developed as anti-fungal treatments targeted against $\beta$-glucan (lipopeptides, e.g. echinocandins and pneumocandins (Kurtz, M. B. & Douglas, C. M. (1997) J. Med. Vet. Myc. 35, 79–86.)) and chitin (e.g. nikkomycin Z (Obi, K. Uda, J. Iwase, K. Sugimoto, O. Ebisu, H. & Matsuda, A. (2000) Bioorg. Med. Chem. Lett. 10, 1451–4)) synthesis.

The mannoproteins represent the remaining content of the wall. They form radially extending fibrillae at the outside of the cell wall and are believed to confer the cell surface properties involved in adhesion and host interactions. A number of classes of mannoproteins have been identified (e.g. Sed1, Flo11, Aga1, Pir2, Als1, Ax12) and these have been separated into groups dependent upon the nature of their attachment to the other cell wall components (Kapteyn, J. C. Hoyer, L. L. Hecht, J. E. Muller, W. H. Andel, A. Verkleij, A. J. Makarow, M. Van Den Ende, H. & Klis, F. M. (2000) Mol. Microbiol. 35, 601–11). During their secretion from the cell some receive a GPI anchor and all become mannosylated. Mannosylation of these proteins is divided into two categories: O- and N-linked. The N-linked are attached via asparagine residues and form extensive branched structures consisting of an $\alpha$1,6 backbone to which $\alpha$1,2-, $\alpha$1,3- and $\beta$1,2-side chains are attached. The O-linked are attached via serine or threonine residues and consist of short linear chains. The extension of both chain types is catalysed by a family of mannosyltransferases. The initial mannose residue is added to serine or threonine by a protein:mannosyl transferase (PMT) which uses dolicholphospho-mannose as a donor of the mannose. Seven PMT's have been reported in *S. cerevisiae* (Strahl-Bolsinger, S. Gentzsch, M. & Tanner, W. (1999) Biochim. Biophys. Acta. 1426, 297–307) and by homology five have been identified to date in Candida (homologues have also been found in Aspergillus and other fungal species). It appears that members of the family show some substrate specificity (Sanders, S. L. Gentzsch, M. Tanner, W. & Herskowitz, I. (1999) J. Cell. Biol. 145, 1177–88) but this has not been clearly defined.

Although a human homologue has been found and evidence of O-mannosylation in some tissues, no activity has been recorded in mammalian tissue.

Deletion of both copies of the PMT1 gene from *Candida albicans* results in a strain that is no longer virulent in animal models (Timpel, C. Strahl-Bolsinger, S. Ziegelbauer, K. & Ernst, J. F. (1998) J. Biol. Chem. 273, 20837–46). The strain also shows a failure to form pseudohyphae under conditions of nitrogen starvation and increased sensitivity to agents associated with cell wall defects.

Without being bound by scientific theory it is proposed that the compounds of the invention inhibit the protein mannosyl transferase enzyme, preventing the formation of the O-linked mannoproteins and compromising the integrity of the fungal cell wall. Defects in the wall structure have been shown to result in cell swelling and ultimately death through rupture.

All preferred features of the first, second and third aspects of the invention also apply to the fourth aspect.

A fifth aspect of the invention provides the use of a compound of formula I or a salt thereof in the manufacture of a medicament for use as an antifungal agent.

For the purposes of this invention, the medicament can be used in the curative or prophylatic treatment of fungal infections in humans and animals.

The medicament comprising one or more compound of formula I will usually be supplied as part of a sterile, pharmaceutical composition which will normally include a pharmaceutically acceptable carrier. This pharmaceutical composition may be in any suitable form as described in the second aspect of the invention, depending on the desired method of administering it to a patient.

It may be provided in unit dosage form, will generally be provided in a sealed container and may be provided as part of a kit. Such a kit would normally (although not necessarily) include instructions for use. It may include a plurality of said unit dosage forms.

All preferred aspects of the first, second, third and fourth aspects of the invention also apply to the fifth aspect.

A sixth aspect of the invention provides a method of treatment for treating an individual suffering from a fungal infection comprising administering to the individual a compound of the first aspect of the invention. The treatment may be prophylactic or in respect of an existing condition.

The compound of the first aspect can be administered as a pharmaceutical composition in combination with a pharmaceutically acceptable excipient as described in the second aspect of the invention. The pharmaceutical composition can comprise one or more of the compounds of the first aspect.

The method of treatment will provide the compound of the first aspect at an effective dosage of 0.1–750 milligrams/kg/day, preferably 0.1–10 milligrams/kg/day. The compounds can be administered once or more a day, twice a week, weekly, every two weeks or monthly.

The compound or pharmaceutical composition can be administered simultaneously, separately or sequentially with another anti-fungal treatment.

A particular feature of the fifth and sixth aspects is the treatment of individuals who are immunosuppressed as a result of a therapy (e.g. chemotherapy or radiotherapy), organ transplant or an infection (e.g. HIV).

The method can be used to treat topical infections caused by species of fungus including Candida, Trichophyton, Microsporum and Epidermophyton or in mucosal infections caused by species of fungus including *Candida albicans* (e.g. thrush and vaginal candidiasis). The method can also be used in the treatment of infections caused by, for example, species of Candida (e.g. *Candida albicans*), *Cryptococcus neoformans, Aspergillus flavus, Aspergillus fumigatus*, Coccidioides, Paracoccidioides, Histoplasma or Blastomyces.

All preferred features of the first, second, third, fourth and fifth aspects of the invention also apply to the sixth aspect.

The invention will now be illustrated by reference to one or more of the following non-limiting examples.

EXAMPLE 1

Benzyl 2-benzyloxy-5-formylbenzoate

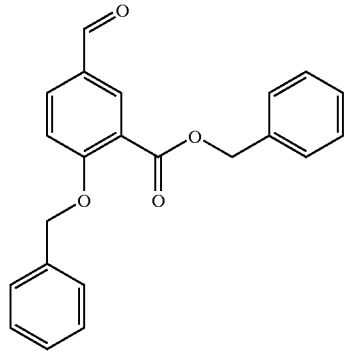

Benzyl bromide (25.6 mL, 0.22 mol, 2.5 eq) was added dropwise to a stirred solution of 5-formylsalicylic acid (10 g, 0.06 mol, 1 eq) and cesium carbonate (84.2 g, 0.26 mol, 3 eq) in N,N-dimethylformamide (150 mL). The reaction mixture was stirred for 3 days and concentrated in vacuo. The residue was dissolved in ethyl acetate (200 mL) and the organic solution washed with water (200 mL) and brine (4×200 mL), then dried over sodium sulfate and evaporated in vacuo. This gave a gummy solid which was recrystallized from ethyl acetate and petroleum ether to give a cream coloured powder (16.1 g, 77%). $R_F$ (petroleum ether:ethyl acetate 1:1) 0.73. $^1$H NMR (CDCl$_3$) δ9.91 (s, 1H, O═C—H), 5.38 (s, 2H, CH$_2$Ph), 5.28 (s, 2H, CH$_2$Ph).

EXAMPLE 2

2-Benzyloxy-5-formylbenzoic acid

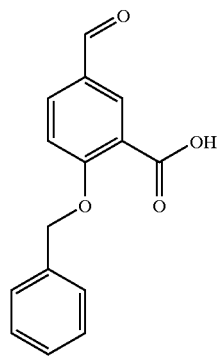

Lithium hydroxide (3.38 g, 0.14 mol, 3 eq) in water (50 mL) was added to a stirred solution of benzyl 2-benzyloxy-5-formylbenzoate (16.13 g, 0.046 mol, 1 eq) in a mixture of tetrahydrofuran (200 mL) and methanol (50 mL). The solution was stirred overnight, acidified to pH 1 with 10% HCl, and the organic solvents removed in vacuo. The aqueous solution was extracted with ethyl acetate (200 mL), and the organic solution washed with brine (200 mL), then extracted with saturated aqueous sodium bicarbonate (3×200 mL). The basic solution was washed with ethyl acetate (200 mL), then acidified to pH 1 with 10% HCl and back extracted with ethyl acetate (3×200 mL). The organic solution was dried over sodium sulfate and evaporated in vacuo to give a pale yellow powder (10.83 g, 89%). $^1$H NMR (CDCl$_3$) δ9.94 (s, 1H, O═C—H), 5.37 (s, 2H, CH$_2$Ph).

EXAMPLE 3

2-Phenylethyl 2-(2-phenylethoxy)-5-formylbenzoate

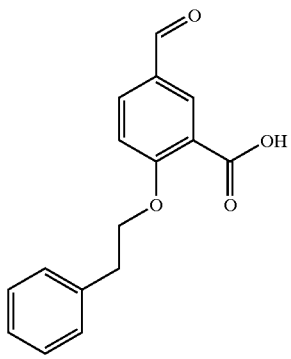

(2-Bromoethyl)benzene (41 mL, 0.3 mol, 5 eq) was added to a stirred solution of 5-formylsalicylic acid (10 g, 0.06 mol, 1 eq), tetra-n-butylammonium iodide (44 g, 0.12 mol, 2 eq) and cesium carbonate (39 g, 0.12 mol, 2 eq) in N,N-dimethylformamide (200 mL). The reaction mixture was stirred for 4 days, then concentrated in vacuo. The residue was diluted with ethyl acetate (200 mL) and the organic solution washed with water (200 mL), 1M HCl (2×200 mL), 1M sodium hydroxide (2×200 mL) and then brine (200 mL), dried over sodium sulfate and evaporated in vacuo to give a brown oil. The product was not purified further, but taken immediately onto the next step. $R_F$ (petroleum ether:ethyl acetate, 1:1) 0.88. $^1$H NMR (CDCl$_3$) δ9.88 (s, 1H, O=C—H), 8.23 (d, 1H, J 2.2 Hz, ArH), 7.98 (dd, 1H, J 8.7 and 2.2 Hz, ArH), 7.06 (d, 1H, J 8.7 Hz, ArH), 4.56 (t, 2H, J 7.2 Hz, OC$\underline{H}_2$CH$_2$Ph), 4.33 (t, 2H, J 7.2 Hz, OC$\underline{H}_2$CH$_2$Ph), 3.11 (t, 2H, J 7.2 Hz, OCH$_2$C$\underline{H}_2$Ph), 3.03 (t, 2H, J 7.2 Hz, OCH$_2$C$\underline{H}_2$Ph).

EXAMPLE 4
2-(2-Phenylethoxy)-5-formylbenzoic acid

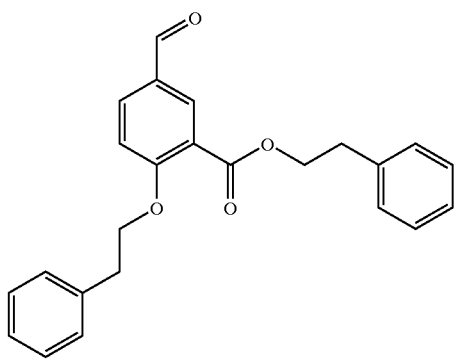

Lithium hydroxide (4.32 g, 0.18 mol, 3 eq) in water (80 mL) was added to a stirred solution of 2-phenylethyl 2-(2-phenylethoxy)-5-formylbenzoate (22.46 g, 0.06 mol, 1 eq) in a mixture of tetrahydrofuran (240 mL) and methanol (80 mL). The reaction mixture was stirred for 3 h, then concentrated in vacuo, and the residue diluted with water (100 mL), and washed with ethyl acetate (2×100 mL). The aqueous solution was acidified to pH 1 with concentrated HCl, extracted with ethyl acetate (2×100 mL), and the organic solution dried over sodium sulfate and evaporated. This gave a gummy solid, which was recrystallized from ethyl acetate and ether to give a pale yellow powder (8.87 g, 55% (2 steps)). $R_F$ (petroleum ether:ethyl acetate, 2:1) 0.35. $^1$H NMR (CDCl$_3$) δ9.97 (s, 1H, O=C—H), 8.65 (d, 1H, J 2.3 Hz, ArH), 8.11 (dd, 1H, J 8.7 and 2.3 Hz, ArH), 7.18 (d, 1H, J 8.7 Hz, ArH), 4.58 (t, 2H, J 6.8 Hz, OC$\underline{H}_2$CH$_2$Ph), 3.27 (t, 2H, J 6.8 Hz, OCH$_2$C$\underline{H}_2$Ph).

EXAMPLE 5
N-phenyl-N-methyl-2-benzyloxy-5-formylbenzamide

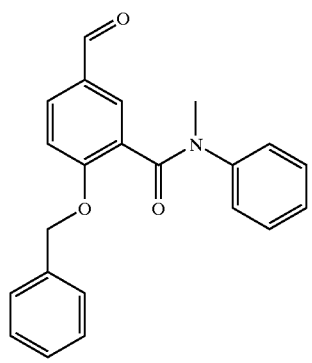

N-Methylaniline (0.18 mL, 1.68 mmol, 2 eq) was added to a solution of 2-benzyloxy-5-formylbenzoic acid (200 mg, 0.84 mmol, 1 eq), 1-hydroxy-7-azabenzotriazole (230 mg, 1.68 mmol, 2 eq), and N-methylmorpholine (0.25 mL, 2.29 mmol, 2.73 eq) in N,N-dimethylformamide (4 mL). To this was added 1-(3-dimethylaminopropyl)-3-ethylcarbodiimide hydrochloride (320 mg, 1.68 mmol, 2 eq) and the reaction mixture stirred overnight. The reaction mixture was diluted with ethyl acetate (20 mL) and washed sequentially with 10% HCl (3×20 mL), brine (20 mL), saturated aqueous sodium bicarbonate (2×20 mL) and brine (20 mL). The organic solution was dried over sodium sulfate and evaporated in vacuo to give a yellow oil (270 mg, 99%). $R_F$ (petroleum ether:ethyl acetate 1:1) 0.73. $^1$H NMR (CDCl$_3$) δ9.79 (s, 1H, O=C—H), 5.01 (s, 2H, CH$_2$Ph), 3.47 (s, 3H, CH$_3$).

The following compounds were prepared by a similar method:

N-(2-Benzyloxy-5-formyl)benzoylmorpholine
1-[(2-Benzyloxy-5-formyl)benzoyl]-4-phenylpiperazine
N,N-Dibenzyl-2-benzyloxy-5-formylbenzamide
1-[(2-Benzyloxy-5-formyl)benzoyl]-4-benzylpiperidine
N,N-Di-n-pentyl-2-benzyloxy-5-formylbenzamide
(S)-N-alpha-Methylbenzyl-N-benzyl-2-benzyloxy-5-formylbenzamide
N,N-Di-n-butyl-2-benzyloxy-5-formylbenzamide
N-n-Butyl-N-benzyl-2-benzyloxy-5-formylbenzamide
(R)-N-alpha-methylbenzyl-2-benzyloxy-5-formylbenzamide
(S)-N-methyl-N-alpha-methylbenzyl-2-benzyloxy-5-formylbenzamide
N,N-Di-n-pentyl-2-(2-phenylethoxy)-5-formylbenzamide.

EXAMPLE 6
(R)-N-Benzyl-N-α-(hydroxymethyl)benzyl-2-benzyloxy-5-formylbenzamide

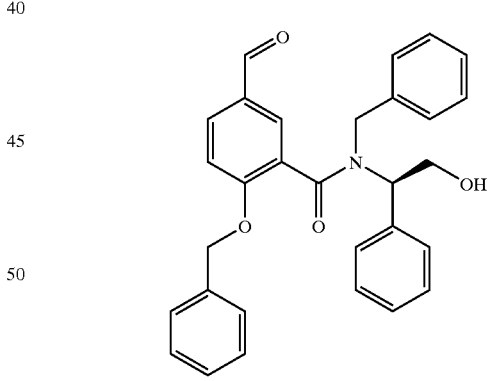

(R)-N-Benzyl-N-α-(hydroxymethyl)benzyl-2-benzyloxy-5-formylbenzamide was prepared from 2-benzyloxy-5-formylbenzoic acid (500 mg, 1.95 mmol, 1 eq) via the same procedure as in Example 5. After work-up, the residue was purified by chromatography on silica gel. Elution with petroleum ether:ethyl acetate (3:1) gave the product as a colourless oil (270 mg, 30%). $R_F$ (petroleum ether:ethyl acetate, 1:1) 0.65. $^1$H NMR (CDCl$_3$) δ9.91 (s, 1H, O=C—H), 8.29 (d, 1H, J 2.1 Hz, ArH), 7.99 (dd, 1H, J 8.7 and 2.2 Hz, ArH), 7.13 (d, 1H, J 8.7 Hz, ArH), 5.25 (s, 2H, OCH$_2$Ph), 4.51 (dd, 1H, J 10.9 and 4.4 Hz, NCHC$\underline{H}_2$), 4.41 (dd, 1H, J 10.9 and 8.4 Hz, NCHC$\underline{H}_2$), 4.14 (m, 1H, NC$\underline{H}$CH$_2$), 3.72 (d, 1H, J 13.4 Hz, NCH$_2$Ph), 3.53 (d, 1H, J 13.4 Hz, NCH$_2$Ph), 2.15 (broad s, 1H, OH).

EXAMPLE 7

Methyl 2-methoxy-5-formylbenzoate

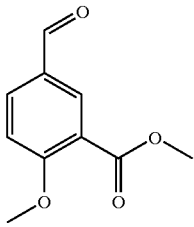

Methyl iodide (3.6 mL, 0.042 mol, 3.5 eq) was added dropwise to a stirred solution of 5-formylsalicylic acid (2.78 g, 0.017 mol, 1 eq) and cesium carbonate (16.36 g, 0.050 mol, 3 eq) in N,N-dimethylformamide (50 mL). The reaction mixture was stirred overnight, then diluted with ethyl acetate (100 mL) and the organic solution washed with water (100 mL), and brine (4×100 mL). The organic solution was dried over sodium sulfate and evaporated in vacuo to a cream coloured powder (2.8 g, 86%). $^1$H NMR (CDCl$_3$) δ9.92 (s, 1H, O=C—H), 4.01 (s, 3H, CH$_3$), 3.93 (s, 3H, CH$_3$).

EXAMPLE 8

2-Methoxy-5-formylbenzoic acid

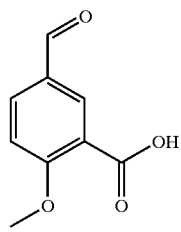

Lithium hydroxide (1.04 g, 0.043 mol, 3 eq) in water (10 mL) was added to a stirred solution of methyl 2-methoxy-5-formylbenzoate (2.8 g, 0.014 mol, 1 eq) in a mixture of tetrahydrofuran (30 mL) and methanol (20 mL). The solution was stirred overnight, acidified to pH 1 with 10% HCl and the organic solvents removed in vacuo. The aqueous solution was extracted with ethyl acetate (100 mL) and the organic solution washed with brine (100 mL), then extracted with saturated aqueous sodium bicarbonate (3×100 mL). The basic solution was washed with ethyl acetate (100 mL), then acidified to pH 1 with 10% HCl and back extracted with dichloromethane (3×100 mL). The organic solution was dried over sodium sulfate and evaporated in vacuo to give a cream coloured powder (2.01 g, 77%). $^1$H NMR (CDCl$_3$) δ9.99 (s, 1H, O=C—H), 4.14 (s, 3H, CH$_3$).

EXAMPLE 9

N,N-di-n-pentyl-2-methoxy-5-formylbenzamide

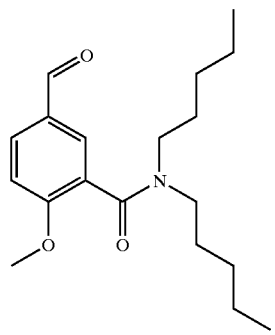

Di-n-pentylamine (873 mg, 5.55 mmol, 2 eq) was added to a solution of 2-methoxy-5-formylbenzoic acid (500 mg, 2.78 mmol, 1 eq), 1-hydroxy-7-azabenzotriazole (755 mg, 5.55 mmol, 2 eq), and N-methylmorpholine (0.83 mL, 7.58 mmol, 2.73 eq) in N,N-dimethylformamide (10 mL). To this was added 1-(3-dimethylaminopropyl)-3-ethylcarbodiimide hydrochloride (1.06 g, 5.55 mmol, 2 eq) and the reaction mixture stirred overnight. The reaction mixture was diluted with ethyl acetate (20 mL) and washed sequentially with 10% HCl (3×20 mL), brine (20 mL), saturated aqueous sodium bicarbonate (2×20 mL) and brine (20 mL). The organic solution was dried over sodium sulfate and evaporated in vacuo to give the product as a pale brown oil (886 mg, 99%). $^1$H NMR (CDCl$_3$) δ9.83 (s, 1H, O=C—H), 3.85 (s, 3H, OCH$_3$), 3.52 (m, 1H, NCH$_2$), 3.38 (m, 1H, NCH$_2$), 2.98 (m, 2H, NCH$_2$).

(S)-N-alpha-Methylbenzyl-N-benzyl-2-methoxy-5-formylbenzamide was prepared by a similar procedure.

EXAMPLE 10

N,N-Di-n-pentyl-2-hydroxy-5-formylbenzamide

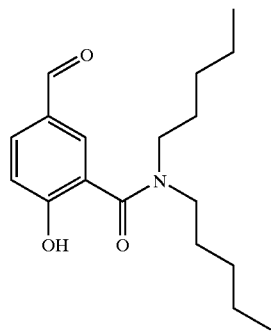

N,N-Di-n-pentyl-2-hydroxy-5-formylbenzamide was prepared from 5-formylsalicylic acid (250 mg, 1 eq) using the same procedure as for N,N-di-n-pentyl-2-methoxy-5-formylbenzamide. The product was obtained as pale brown oil (211 mg, 46%). $^1$H NMR (CDCl$_3$) δ9.67 (s, 1H, O=C—H), 3.33 (m, 4H, NCH$_2$).

EXAMPLE 11
N-benzyl-N-phenyl-2-benzyloxy-5-formylbenzamide

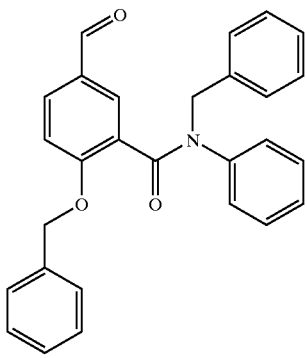

N-Phenylbenzylamine (0.72 g, 3.9 mmol, 2 eq) was added to a solution of 2-benzyloxy-5-formylbenzoic acid (500 mg, 1.95 mmol, 1 eq), 1-hydroxy-7-azabenzotriazole (530 mg, 3.9 mmol, 2 eq), and N-methylmorpholine (0.58 mL, 5.3 mmol, 2.73 eq) in N,N-dimethylformamide (10 mL). To this was added 1-(3-dimethylaminopropyl)-3-ethylcarbodiimide hydrochloride (750 mg, 13.9 mmol, 2 eq) and the stirred reaction mixture was heated overnight at 50° C. The reaction mixture was diluted with ethyl acetate (20 mL) and washed sequentially with 10% HCl (3×20 mL), brine (20 mL), saturated aqueous sodium bicarbonate (2×20 mL) and brine (20 mL). The organic solution was dried over sodium sulfate and evaporated in vacuo. The residue was chromatographed on silica with petroleum ether:ethyl acetate (3:1) as eluent, to give the product as a white powder (300 mg, 37%). $R_F$ (petroleum ether:ethyl acetate 1:1) 0.55. $^1$H NMR (CDCl$_3$) δ9.78 (s, 1H, O=C—H), 5.08 (s, 2H, OCH$_2$Ph), 5.02 (s, 2H, NCH$_2$Ph).

EXAMPLE 12
2,4-Difluorobenzyl 2-(2,4-difluorobenzyloxy)-5-formylbenzoate

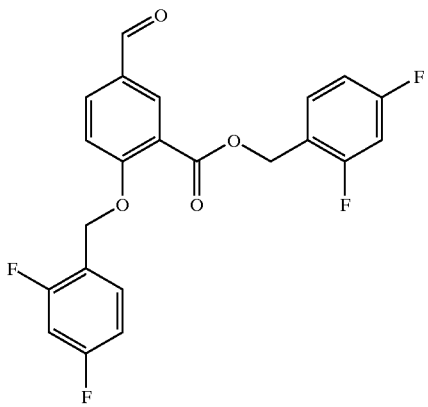

2,4-Difluorobenzyl bromide (0.77 mL, 6 mmol, 1 eq) was added dropwise to a stirred solution of 5-formylsalicylic acid (1 g, 6 mmol, 1 eq) and cesium carbonate (5.87 g, 18 mmol, 3 eq) in N,N-dimethylformamide (30 mL). The reaction mixture was diluted with ethyl acetate (50 mL) and the organic solution washed with water (50 mL), saturated aqueous sodium bicarbonate (2×50 mL) and brine (50 mL), then dried over sodium sulfate and evaporated in vacuo to give the product as a white powder (1.2 g, 50%). $^1$H NMR (CDCl$_3$) δ9.91 (s, 1H, O=C—H), 5.37 (s, 2H, CH$_2$Ar), 5.25 (s, 2H, CH$_2$Ar).

EXAMPLE 13
2-(2,4-Difluorobenzyloxy)-5-formylbenzoic acid

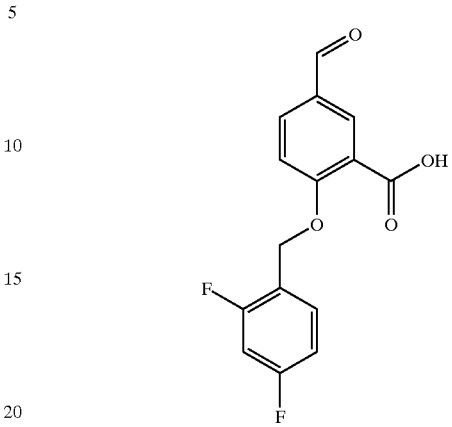

2-(2,4-Difluorobenzyloxy)-5-formylbenzoic acid was prepared from 2,4-difluorobenzyl 2-(2,4-difluorobenzyloxy)-5-formylbenzoate (1.2 g, 1 eq) using the same procedure as for 2-benzyloxy-5-formylbenzoic acid. The product was obtained as a white powder (746 mg, 89%). $^1$H NMR (CDCl$_3$) δ9.97 (s, 1H, O=C—H), 5.37 (s, 2H, CH$_2$Ar).

EXAMPLE 14
N,N-Di-n-pentyl-2-(2,4-difluorobenzyloxy)-5-formylbenzamide

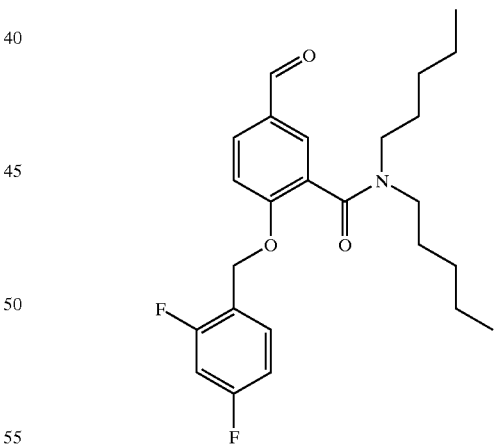

N,N-Di-n-pentyl-2-(2,4-difluorobenzyloxy)-5-formylbenzamide was prepared from 2-(2,4-difluorobenzyloxy)-5-formylbenzoic acid (200 mg, 1 eq) using the same procedure as for N,N-di-n-pentyl-2-methoxy-5-formylbenzamide. The product was obtained as a pale brown oil (442 mg, 99%). $^1$H NMR (CDCl$_3$) δ9.89 (s, 1H, O=C—H), 5.22 (d, 1H, CH$_2$Ar), 5.10 (d, 1H, CH$_2$Ar), 3.74 (m, 1H, NCH$_2$), 3.14 (m, 1H, NCH$_2$), 3.05 (m, 2H, NCH$_2$).

EXAMPLE 15

Preparation of 4-Trifluoromethylbenzyl 2-(4-trifluoromethylbenzyl-oxy)-5-formylbenzoate

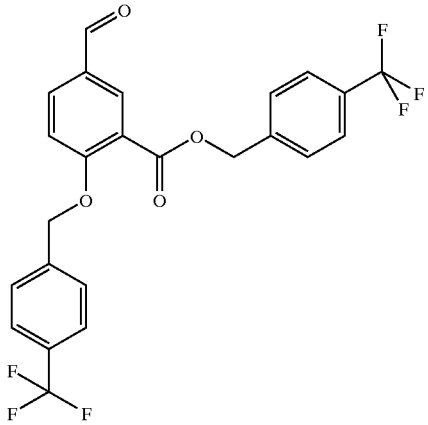

4-Trifluoromethylbenzyl 2-(4-trifluoromethylbenzyloxy)-5-formylbenzoate was prepared from using the same procedure as for 2,4-difluorobenzyl 2-(2,4-difluorobenzyloxy)-5-formylbenzoate. The product was obtained as a white powder (1.41 g, 50%). $^1$H NMR (CDCl$_3$) δ9.91 (s, 1H, O=C—H), 5.42 (s, 2H, CH$_2$Ar), 5.31 (s, 2H, CH$_2$Ar).

EXAMPLE 16

2-(4-Trifluoromethylbenzyloxy)-5-formylbenzoic acid

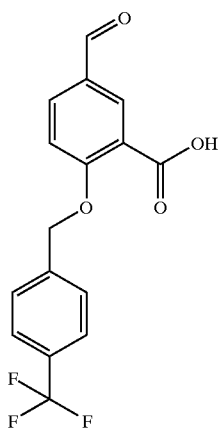

2-(4-Trifluoromethylbenzyloxy)-5-formylbenzoic acid was prepared from 4-trifluoromethylbenzyl 2-(4-trifluoromethylbenzyloxy)-5-formylbenzoate (1.41 g, 1 eq) using the same procedure as for 2-benzyloxy-5-formylbenzoic acid. The product was obtained as a white powder (764 mg, 67%). $^1$H NMR (CDCl$_3$) δ9.97 (s, 1H, O=C—H), 5.41 (s, 2H, CH$_2$Ar).

EXAMPLE 17

N,N-Di-n-pentyl-2-(4-trifluoromethylbenzyloxy)-5-formylbenzamide

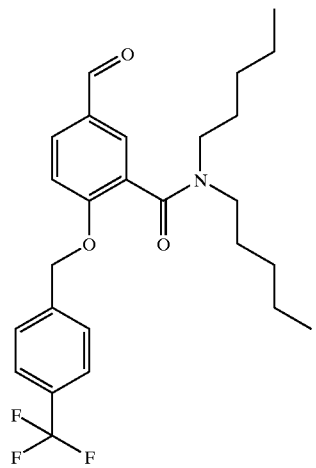

N,N-Di-n-pentyl-2-(4-trifluoromethylbenzyloxy)-5-formylbenzamide was prepared from 2-(4-trifluoromethylbenzyloxy)-5-formylbenzoic acid (300 mg, 1 eq) using the same procedure as for N,N-di-n-pentyl-2-methoxy-5-formylbenzamide. The product was obtained as a pale brown oil (424 mg, 99%). $^1$H NMR (CDCl$_3$) δ9.88 (s, 1H, O=C—H), 5.21 (s, 2H, CH$_2$Ar), 3.72 (m, 1H, NCH$_2$), 3.20 (m, 1H, NCH$_2$), 3.05 (m, 2H, NCH$_2$).

EXAMPLE 18

3-Benzyloxy-4-trifluoromethanesulfonylbenzaldehyde

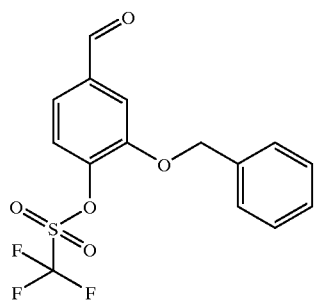

Trifluoromethanesulfonic anhydride (4.4 mL, 26.3 mmol, 1.2 eq) was added dropwise to an ice-cold solution of 3-benzyloxy-4-hydroxybenzaldehyde (5 g, 21.9 mmol, 1 eq) in anhydrous pyridine (100 mL). The solution was stirred for 4 h and then concentrated in vacuo. The residue was dissolved in ethyl acetate (100 mL) and washed with 10% HCl (2×100 mL), saturated aqueous sodium bicarbonate (200 mL) and brine (200 mL). The organic solution was dried over sodium sulfate and evaporated in vacuo to give the product as a dark brown oil (7.37 g, 91%). $^1$H NMR (CDCl$_3$) δ9.97 (s, 1H, O=C—H), 5.27 (s, 2H, OCH$_2$Ph).

EXAMPLE 19

2-Benzyloxy-4-formylbenzoic acid

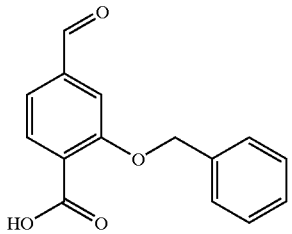

A mixture of 3-benzyloxy-4-trifluoromethanesulfonylbenzaldehyde (350 mg, 0.97 mmol, 1 eq), potassium acetate (380 mg, 3.89 mmol, 4 eq), palladium (II) diacetate (32 mg, 0.05 mmol, 0.05 eq) and 1,1'-bis-(diphenylphosphino)ferrocene (dppf) (108 mg, 0.19 mmol, 0.2 eq) in anhydrous dimethylsulfoxide (6 mL) was purged with carbon monoxide and stirred for 5 min. The reaction mixture was then heated to 60□C. and stirred under a carbon monoxide balloon for 3 h. The solution was allowed to cool to room temperature, and acidified to pH 1 with 10% HCl and then extracted with ethyl acetate (2×20 mL). The organic extracts were combined and washed with brine, then extracted with saturated aqueous sodium bicarbonate (3×20 mL). The aqueous extracts were combined, washed with ethyl acetate (2×20 mL), acidified to pH 1 with 10% HCl and back extracted with ethyl acetate (2×20 mL). The organic solution was dried over sodium sulfate and evaporated in vacuo to give a cream coloured powder (146 mg, 59%). $^1$H NMR (CDCl$_3$) δ10.08 (s, 1H, O=C—H), 5.39 (s, 2H, OCH$_2$Ph).

EXAMPLE 20

N,N-Dibenzyl-2-benzyloxy-4-formylbenzamide

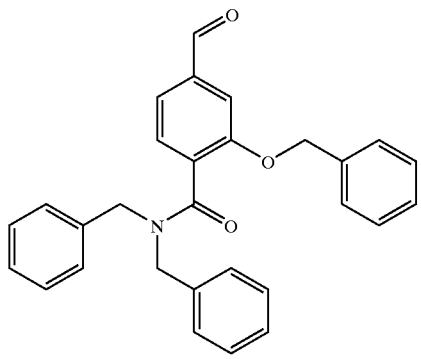

N,N-dibenzyl-2-benzyloxy-4-formylbenzamide was prepared from 2-benzyloxy-4-formylbenzoic acid (146 mg, 1 eq) and dibenzylamine (0.22 mL, 2 eq) using the same procedure as for N-phenyl-N-methyl-2-benzyloxy-5-formylbenzamide. The product was obtained as a brown oil (236 g, 95%). $^1$H NMR (CDCl$_3$) δ9.96 (s, 1H, O=C—H), 5.24 (m, 3H, OCH$_2$Ph and NCH$_2$Ph), 4.33 (d, 1H, NCH$_2$Ph), 4.11 (m, 2H, NCH$_2$Ph).

EXAMPLE 21

3-[[(Methylsulfonyl)oxy]methyl]-4-(phenylmethoxy)benzaldehyde

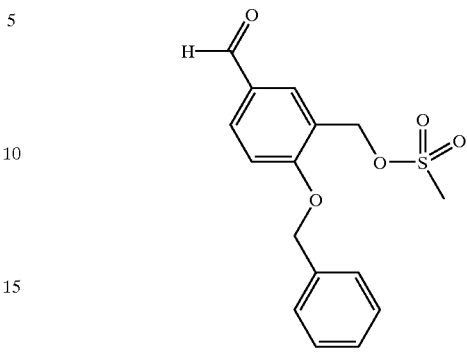

Methanesulfonyl chloride (2.50 g) was added to a stirred solution of 3-(hydroxymethyl)-4-phenylmethoxybenzaldehyde (4.00 g) in dichloromethane (50 ml) at 0° C. To this solution was then added diisopropylethylamine (8.1 ml) over approx. 2 minutes. After stirring for a further 5 minutes the reaction mixture was partitioned between dichloromethane and water. The organic layer was washed with dilute hydrochloric acid, dried over sodium sulfate, filtered and concentrated under reduced pressure to give pale straw coloured oil. Addition of diethyl ether caused the product to crystallize. This material was collected and washed with more diethyl ether to give 3-[[(methylsulfonyl)oxy]methyl]-4-phenylmethoxybenzaldehyde (4.51 g) as off-white crystals. $^1$H NMR (CDCl$_3$) δ9.78 (s, 1H, CHO); 5.22 (s, 2H); 5.10 (s, 2H); 2.83 (s, 3H). TLC (silica gel): R$_f$=0.4 (dichloromethane: diethyl ether, 24:1).

EXAMPLE 22

3-[(Dipentylamino)methyl]-4-phenylmethoxybenzaldehyde

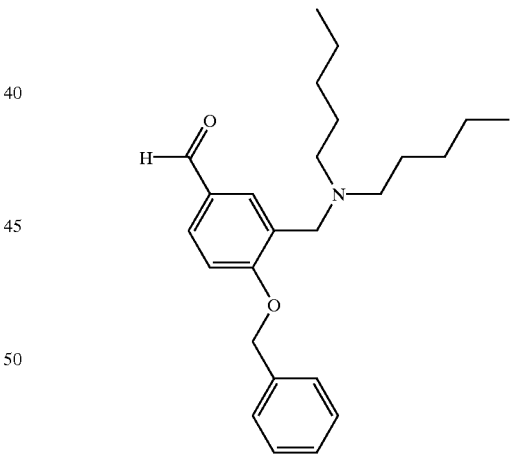

To a solution of dipentylamine (258 mg) and diiosopropylethylamine (212 mg) in dimethylformamide (2 ml) was added 3-[[(methylsulfonyl)oxy]methyl]-4-phenylmethoxybenzaldehyde (350 mg). After stirring at room temperature for 2 weeks, the reaction mixture was partially concentrated under reduced pressure and the residue was purified by flash column chromatography using petroleum ether:diethyl ether (1:3) as eluant. The pure fractions were combined and evaporated under reduced pressure to give 3-[(dipentylamino)methyl]-4-phenylmethoxybenzaldehyde (356 mg) as a gum. $^1$H NMR (CDCl$_3$) δ9.90 (s, 1H, CHO); 5.15 (s, 2H); 3.70 (s, 2H); 2.50 (m, 4H); 1.55 (m, 4H); 1.30(m, 8H); 0.90 (t, 6H).

EXAMPLE 23
4-Phenylmethoxy-3-[[N-phenylmethyl-N-(2-phenylethyl)amino]-methyl]benzaldehyde

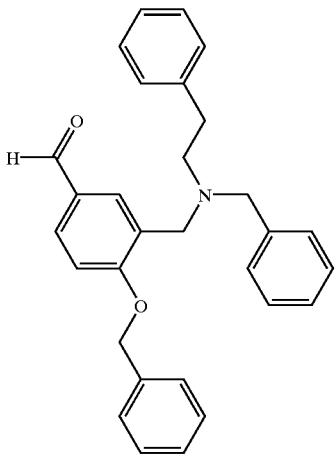

To a solution of N-benzyl-N-(2-phenylethyl)amine (351 mg) and diisopropyl-ethylamine (145 mg) in dimethylformamide (1.5 ml) was added 3-[[(methylsulfonyl)oxy]methyl]-4-phenylmethoxybenzaldehyde (355 mg). After stirring at room temperature for 3 hours, the reaction mixture was partially concentrated under reduced pressure and the residue was purified by flash chromatography column using petroleum ether:diethyl ether (1:3) as eluant. The pure fractions were combined and evaporated under reduced pressure to give 4-phenylmethoxy-3-[[N-phenylmethyl-N-(2-phenylethyl)amino]methyl]benzaldehyde (420 mg) as a gum. $^1$H NMR (CDCl$_3$) δ9.89 (s, 1H, CHO); 5.20 (s, 2H); 3.88 (s, 2H); 3.85 (s, 2H); 2.92 (m, 4H, C$\underline{H}_2$C$\underline{H}_2$).

EXAMPLE 24
4-Phenylmethoxy-3-[[(N,N-di-(phenylmethyl)amino]methyl]-benzaldehyde

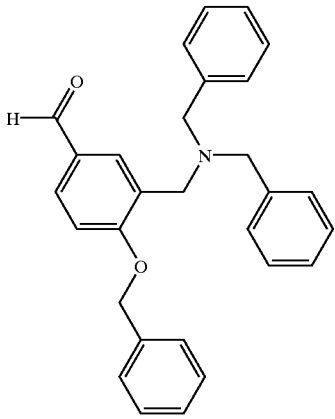

To a solution of dibenzylamine (370 mg) and diisopropylethylamine (130 mg) in dimethylformamide (1.2 ml) was added 3-[[(methylsulfonyl)oxy]methyl]-4-phenylmethoxybenzaldehyde (500 mg). After stirring at room temperature for 3 hours, the reaction mixture was partially concentrated under reduced pressure and the residue was purified by flash column chromatography using petroleum ether:diethyl ether (1:3) as eluant. The pure fractions were combined and evaporated under reduced pressure to give 4-phenylmethoxy-3-[[(N,N-di-(phenylmethyl)amino]-methyl]benzaldehyde (500 mg) as a gum. $^1$H NMR (CDCl$_3$) δ10.01 (s, 1H, CHO); 5.23 (s, 2H); 3.79 (s, 2H); 3.71 (s, 4H). TLC (silica gel): R$_f$=0.7 (Petroleum ether:diethyl ether, 1:3).

EXAMPLE 25
4-Phenylmethoxy-3-[[(4-phenyl)-1-piperazinyl]methyl]benzaldehyde

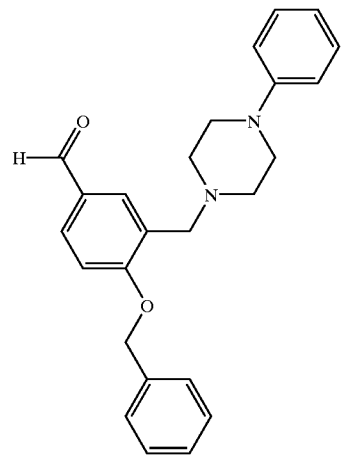

To a solution of N-phenylpiperazine (200 mg) and diiosopropylethylamine (130 mg) in dimethylformamide (1 ml) was added 3-[[(methylsulfonyl)oxy]methyl]-4-phenylmethoxybenzaldehyde (320 mg). After stirring at room temperature for 3 hours the reaction mixture was partially concentrated under reduced pressure and the residue was purified by flash chromatography column using petroleum ether:diethyl ether (1:3) as eluant. The pure fractions were combined and evaporated under reduced pressure to give a gum which was crystallized from diethyl ether to give 4-phenylmethoxy-3-[[(4-phenyl)-1-piperazinyl]methyl]benzaldehyde (320 mg) as white crystals. $^1$H NMR (CDCl$_3$) δ9.95 (s, 1H, CHO); 5.23 (s, 2H); 3.80 (s, 2H); 3.30 (m, 4H); 2.78 (m, 4H). TLC (silica gel): R$_f$=0.7 (petroleum ether:diethyl ether, 1:4).

EXAMPLE 26
4-Phenylmethoxy-3-[[[N-(phenylmethyl)-N-ethyl]amino]methyl]-benzaldehyde

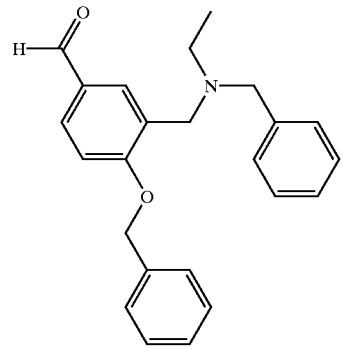

To a solution of N-benzyl-N-ethylamine (225 mg) and diisopropylethylamine (144 mg) in dimethylformamide (1.5 ml) was added 3-[[(methylsulfonyl)oxy]methyl]-4-phenylmethoxybenzaldehyde (355 mg). After stirring at room temperature for 3 hours the reaction mixture was partially concentrated under reduced pressure and the residue was purified by flash column chromatography using petroleum ether:diethyl ether (1:3) as eluant. The pure fractions were combined and evaporated under reduced pressure to give 4-phenylmethoxy-3-[[[N-(phenylmethyl)-N-ethyl]amino]methyl]benzaldehyde (344 mg) as a gum. $^1$H NMR (CDCl$_3$) δ10.06 (s, 1H, CHO); 5.24 (s, 2H); 3.89 (s, 2H); 3.81 (s, 2H); 2.73 (q, 2H, C$\underline{H}_2$CH$_3$); 1.27 (t, 3H, CH$_2$C$\underline{H}_3$). TLC (silica gel): R$_f$=0.6 (Petroleum ether:diethyl ether, 1:3).

EXAMPLE 27

4-Phenylmethoxy-3-[[4-(phenylmethyl)-1-piperidinyl]methyl]-benzaldehyde

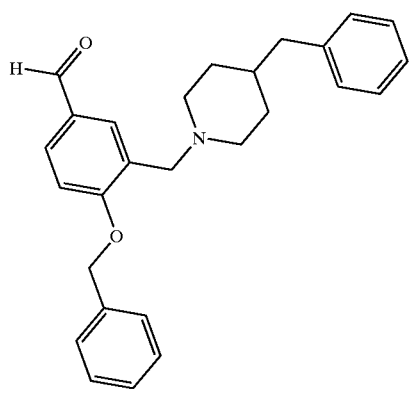

To a solution of 4-(phenylmethyl)piperidinyl (200 mg) and diisopropylethylamine (130 mg) in dimethylformamide (1 ml) was added 3-[[(methylsulfonyl)oxy]methyl]-4-phenylmethoxybenzaldehyde (320 mg). After stirring at room temperature for 3 hours the reaction mixture was partially concentrated under reduced pressure and the residue was purified by flash column chromatography using petroleum ether:diethyl ether (1:1) as eluant. The pure fractions were combined and evaporated under reduced pressure to give 4-phenylmethoxy-3-[[4-(phenylmethyl)-1-piperidinyl]-methyl]benzaldehyde (170 mg) as a gum. $^1$H NMR (CDCl$_3$) δ9.95 (s, 1H, CHO); 5.20 (s, 2H); 3.68 (s, 2H). TLC (silica gel): R$_f$=0.2 (dichloromethane: diethyl ether, 3:1).

EXAMPLE 28

5-[[[3-(Phenylmethoxy)carbonyl-4-(phenylmethoxy)]phenyl]-methylene]-4-oxo-2-thioxo-3-thiazolidineacetic acid

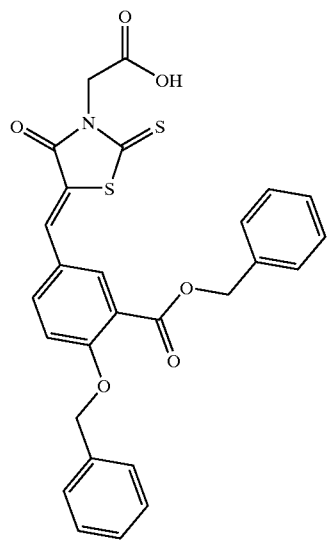

A solution of rhodanine-3-acetic acid (200 mg, 1.05 mmol, 1 eq), benzyl 2-benzyloxy-5-formylbenzoate (430 mg, 1.26 mmol, 1.2 eq) and sodium acetate (257 mg, 3.14 mmol, 3 eq) in acetic acid (10 ml) was heated to reflux (150□C.) and stirred overnight. As the reaction mixture cooled to room temperature the product precipitated and it was collected by filtration and washed with acetic acid, then petroleum ether, suspended in water and freeze-dried overnight in vacuo to give a yellow powder (379 mg, 70%) mp 184–188° C.: $^1$H NMR (d6 DMSO) δ7.91 (s, 1H, C═C—H), 5.33 (s, 2H, CH$_2$Ph), 5.30 (s, 2H, CH$_2$Ph), 4.73 (s, 2H, C$\underline{H}_2$CO$_2$H).

EXAMPLE 29

5-[[[3-(N-methyl-N-phenylamino)carbonyl-4-(phenylmethoxy)]-phenyl]methylene]-4-oxo-2-thioxo-3-thiazolidineacetic acid

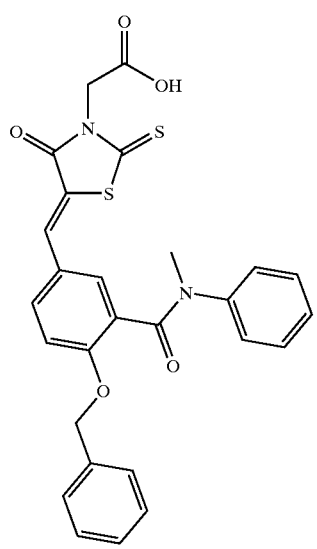

This compound was prepared from N-methyl-N-phenyl-2-benzyloxy-5-formylbenzamide (256 mg, 1.2 eq) using the same procedure as for Example 28 but the product did not precipitate from the reaction mixture. Instead, the reaction mixture was concentrated in vacuo and the residue dissolved in ethyl acetate (20 mL). The organic solution was washed with water (2×20 mL) and extracted with saturated aqueous sodium bicarbonate (3×20 mL). The combined basic extracts were washed with ethyl acetate (20 mL), then acidified to pH 1 with 10% HCl and back extracted with ethyl acetate (2×20 mL). The organic extracts were combined, dried over sodium sulfate and evaporated in vacuo to a gummy solid which was recrystallized from acetone and petroleum ether. The product was suspended in water and freeze-dried overnight in vacuo to give a yellow powder (180 mg, 52%) mp 186–189° C.: $^1$H NMR (d6 DMSO) δ7.72 (s, 1H, C=C—H), 5.14 (s, 2H, CH$_2$Ph), 4.72 (s, 2H, C$\underline{H}_2$CO$_2$H), 3.35 (s, 3H, CH$_3$).

EXAMPLE 30

5-[[[3-(N-morpholinyl)carbonyl-4-(phenylmethoxy)]phenyl]-methylene]-4-oxo-2-thioxo-3-thiazolidineacetic acid

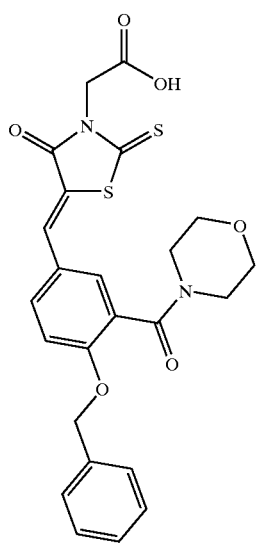

This compound was prepared from N-(2-benzyloxy-5-formylphenyl)carboxy-morpholine (390 mg, 1.2 eq) using the same procedure as for Example 28 and was obtained as a yellow powder (420 mg, 85%) mp 220–224° C.: $^1$H NMR (d6 DMSO) δ7.88 (s, 1H, C=C—H), 5.28 (s, 2H, CH$_2$Ph), 4.74 (s, 2H, C$\underline{H}_2$CO$_2$H).

EXAMPLE 31

5-[[[3-(4-phenyl-1-piperazinyl)carbonyl-4-(phenylmethoxy)]phenyl]-methylene]-4-oxo-2-thioxo-3-thiazolidineacetic acid

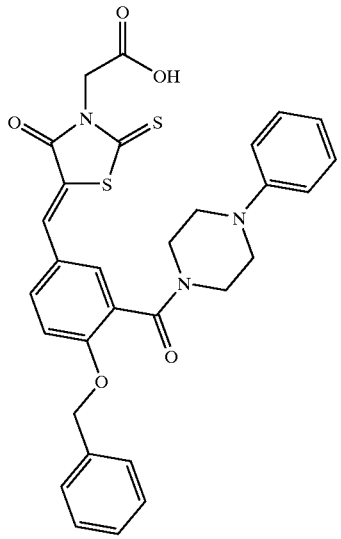

This compound was prepared from 1-[(2-Benzyloxy-5-formyl)benzoyl]-4-phenylpiperazine (480 mg, 1.2 eq) using the same procedure as for Example 28 but the product did not precipitate from the reaction mixture. Instead, the reaction mixture was concentrated in vacuo and the residue chromatographed on silica with petroleum ether:ethyl acetate:acetic acid (49:49:1). This gave a yellow powder which was suspended in water and freeze-dried in vacuo overnight (390 mg, 65%). $^1$H NMR (d6 DMSO) δ7.90 (s, 1H, C=C—H), 5.28 (s, 2H, CH$_2$Ph), 4.74 (s, 2H, C$\underline{H}_2$CO$_2$H).

EXAMPLE 32

5-[[[3-(N,N-Dibenzylamino)carbonyl-4-(phenylmethoxy)]-phenyl]methylene]-4-oxo-2-thioxo-3-thiazolidineacetic acid

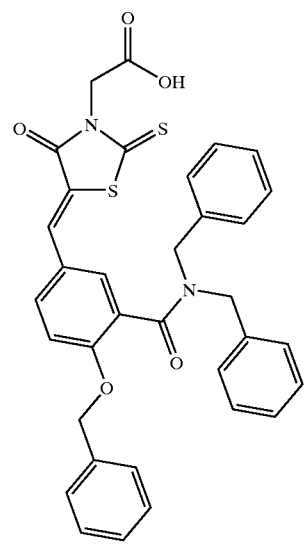

This compound was prepared from N,N-dibenzyl-2-benzyloxy-5-formylphenyl-benzamide (460 mg, 1.2 eq)

using the same procedure as for Example 29 and was obtained as a yellow powder (220 mg, 40%). Mp 197–200° C. ¹HNMR (d6 DMSO) δ7.86 (s, 1H, C=C—H), 5.30 (s, 2H, OCH$_2$Ph), 5.10 (d, 1H, NCH$_2$ Ph), 4.73 (s, 2H, CH$_2$CO$_2$H), 4.40 (d, 1H, NCH$_2$Ph), 4.14 (d, 1H, NCH$_2$Ph), 4.04 (d, 1H, NCH$_2$PH).

EXAMPLE 33
5-[[[3-(4-Benzyl-1-piperidinyl)carbonyl-4-(phenylmethoxy)]phenyl]-methylene]-4-oxo-2-thioxo-3-thiazolidineacetic acid

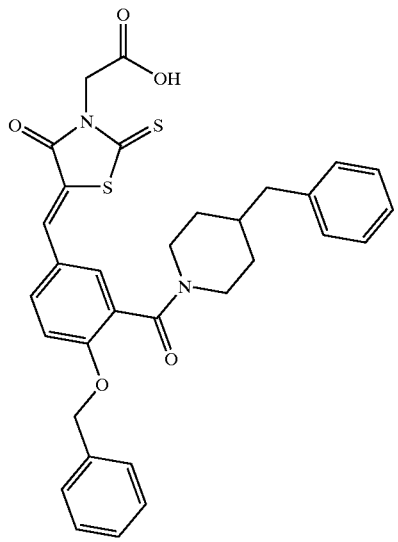

This compound was prepared from 1-[(2-Benzyloxy-5-formyl)benzoyl]-4-benzylpiperidine (490 mg, 1.2 eq) using the same procedure as for Example 28 and as obtained as a yellow powder (340 mg, 58%) mp 189–194° C.: ¹H NMR (d6 DMSO) (rotamers) δ7.86 and 7.84 (2×s, 1H, C=C—H), 5.25 (s, 2H, OCH$_2$Ph), 4.64 and 4.63 (2×s, 2H, CH$_2$CO$_2$H), 4.47 (m, 1H, NCH$_2$Ph), 3.28 (m, 1H, NCH$_2$Ph), 2.90 (m, 1H, NCH$_2$Ph), 2.64 (m, 1H, NCH$_2$Ph), 2.14 (m, 1H, CH).

EXAMPLE 34
5-[[[3-(N,N-Dipentylamino)carbonyl-4-(phenylmethoxy)]-phenyl]methylene]-4-oxo-2-thioxo-3-thiazolidineacetic acid

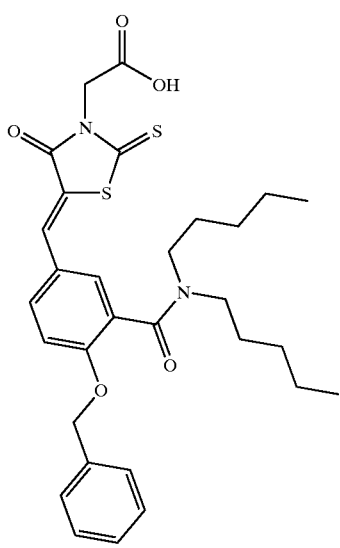

This compound was prepared from N,N-di-n-pentyl-2-benzyloxy-5-formylbenzamide (370 mg, 1.2 eq) using the same procedure as for Example 28 but the product did not precipitate from the reaction mixture. Instead, the reaction mixture was diluted with ethyl acetate (20 mL), and washed with water (2×20 mL). The organic solution was dried over sodium sulfate and evaporated in vacuo to give a gummy solid which was recrystallized from ethyl acetate and petroleum ether. The product was suspended in water and freeze-dried overnight in vacuo to give a yellow powder (290 mg, 65%) mp 211–214° C.: ¹H NMR (d6 DMSO) δ7.89 (s, 1H, C=C—H), 5.24 (s, 2H, CH$_2$Ph), 4.72 (s, 2H, CH$_2$CO$_2$H), 3.66 (dt, 1H, NCH$_2$), 3.06 (m, 3H, NCH$_2$).

EXAMPLE 35

5-[[[3-((S)-N-Benzyl-N-alpha-methylbenzylamino) carbonyl-4-(phenyl-methoxy)]-phenyl]methylene]-4-oxo-2-thioxo-3-thiazolidineacetic acid

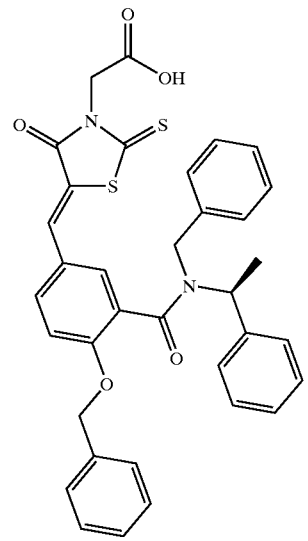

This compound was prepared from (S)-N-benzyl-N-alpha-methylbenzyl-(2-benzyloxy-5-formyl)benzamide (560 mg, 1.2 eq) using the same procedure as for Example 34. The product was recrystallized from ethyl acetate and petroleum ether, and then acetic acid. It was washed with methanol, suspended in water and freeze-dried overnight in vacuo to give a yellow powder (300 mg, 46%) mp 204–209° C.: ¹H NMR (d6 DMSO) (rotamers) δ8.02, 7.95 and 7.75 (3×s, 1H, C=C—H), 5.34 and 5.33 (2×s, 2H, OCH$_2$Ph), 4.73 (s, 2H, CH$_2$CO$_2$H). Anal. Found: C, 67.22; H, 5.07; N, 4.39; S, 9.98. Calcd for $C_{35}H_{30}N_2O_5S_2$ requires C, 67.50; H, 4.86; N, 4.50; S, 10.30.

EXAMPLE 36

5-[[[3-(N,N-Dibutylamino)carbonyl-4-(phenylmethoxy)]-phenyl]methylene]-4-oxo-2-thioxo-3-thiazolidineacetic acid

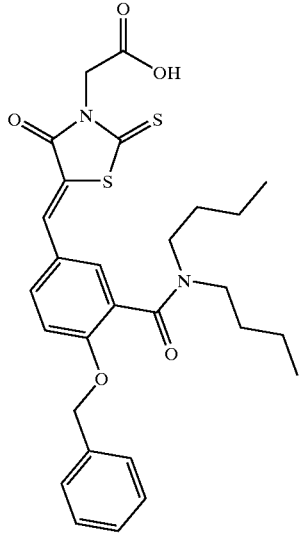

This compound was prepared from N,N-di-n-butyl-2-benzyloxy-5-formyl-benzamide (355 mg, 1 eq) using the same procedure as for Example 28 and was obtained as a yellow powder (221 mg, 39%) mp 200–205° C.: $^1$H NMR (d6 DMSO) δ7.91 (s, 1H, C=C—H), 5.23 (s, 2H, CH$_2$Ph), 4.73 (s, 2H, C$\underline{H}_2$CO$_2$H), 3.69 (dt, 1H, NCH$_2$), 3.06 (m, 3H, NCH$_2$).

EXAMPLE 37

5-[[[3-(N-Benzyl-N-butylamino)carbonyl-4-(phenylmethoxy)]-phenyl]methylene]-4-oxo-2-thioxo-3-thiazolidineacetic acid

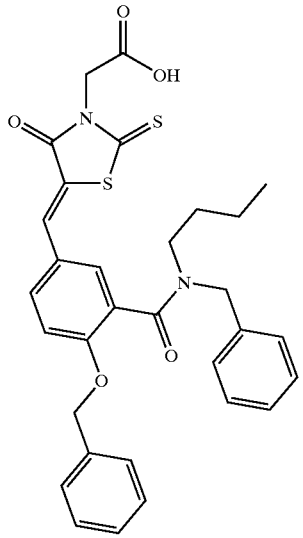

This compound was prepared from N-n-butyl-N-benzyl-2-benzyloxy-5-formylbenzamide (500 mg, 1.2 eq) using the same procedure as for Example 34 and was obtained as a yellow powder (420 mg, 70%). $^1$H NMR (d6 DMSO) δ7.94 and 7.84 (2×s, 1H, C=C—H), 5.28 and 5.26 (2×s, 2H, OCH$_2$Ph), 5.07 (d, 0.5H, NCH$_2$Ph), 4.74 and 4.72 (2×s, 2H, C$\underline{H}_2$CO$_2$H), 4.29 (m, 1.5H, NCH$_2$), 4.02 (m, 0.5H, NCH$_2$), 3.72 (m, 0.5H, NCH$_2$), 3.04 (m, 0.5H, NCH$_2$), 2.92 (m, 0.5H, NCH$_2$).

EXAMPLE 38

5-[[[3-((R)-N-alpha-methylbenzylamino)carbonyl-4-(phenylmethoxy)]-phenyl]methylene]-4-oxo-2-thioxo-3-thiazolidineacetic acid

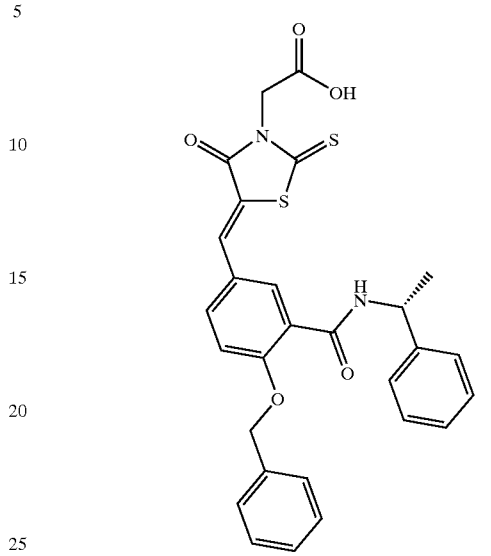

This compound was prepared from (R)-N-alpha-methylbenzyl-2-benzyloxy-5-formylbenzamide (451 mg, 1.2 eq) using the same procedure as for Example 28 and was obtained as a yellow powder (460 mg, 83%) mp 217–221° C.: $^1$H NMR (d6 DMSO) δ8.57 (d, 1H, NH), 7.94 (s, 1H, C=C—H), 5.32 (s, 2H, CH$_2$Ph), 5.06 (m, 1H, C$\underline{H}$CH$_3$), 4.72 (s, 2H, C$\underline{H}_2$CO$_2$H), 1.27 (d, 3H, CHC$\underline{H}_3$).

EXAMPLE 39

5-[[[3-((S)-N-methyl-N-alpha-methylbenzylamino)carbonyl-4-(phenylmethoxy)]-phenyl]methylene]-4-oxo-2-thioxo-3-thiazolidineacetic acid

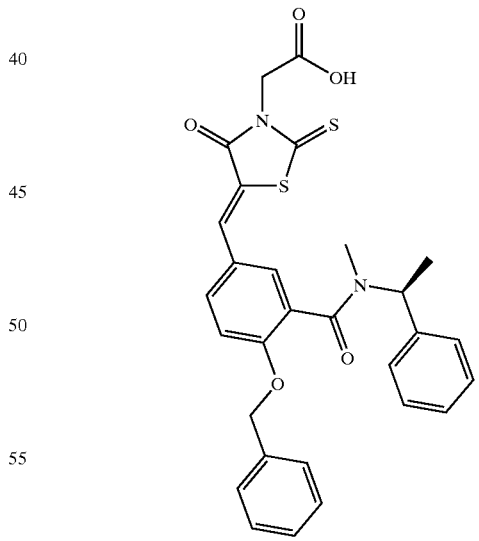

This compound was prepared from (S)-N-methyl-N-alpha-methylbenzyl-2-benzyloxy-5-formylbenzamide (470 mg, 1.2 eq) using the same procedure as for Example 34 and was obtained as a yellow powder (380 mg, 74%) mp 181–184° C.: $^1$H NMR (d6 DMSO) (rotamers) δ7.93, 7.90 and 7.86 (3×s, 1H, C=C—H), 5.33, 5.26 and 5.26 (3×s, 2H, CH$_2$Ph), 5.90 and 5.29 (2×m, 1H, CHC$\underline{H}_3$), (4.75 and 4.72 (2×s, 2H, C$\underline{H}_2$CO$_2$H), 2.71, 2.50 and 2.43 (3×s, 3H, NCH$_3$), 1.52, 1.45 and 1.34 (3×d, 3H, CHC$\underline{H}_3$).

EXAMPLE 40

5-[[[3-(N-Benzyl-N-phenylamino)carbonyl-4-(phenylmethoxy)]-phenyl]methylene]-4-oxo-2-thioxo-3-thiazolidineacetic acid

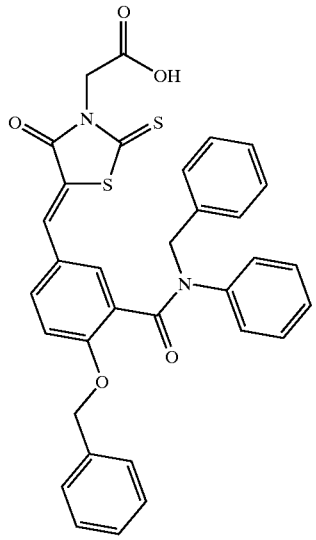

This compound was prepared from N-benzyl-N-phenyl-2-benzyloxy-5-formylbenzamide (300 mg, 1.2 eq) using the same procedure as for Example 28 but the product did not precipitate from the reaction mixture. Instead, the reaction mixture was diluted with ethyl acetate (20 mL), and washed with water (2×20 mL). The organic solution was dried over sodium sulfate and evaporated in vacuo. The product was chromatographed on silica with petroleum ether:ethyl acetate:acetic acid (33:16:1) as eluent, then suspended in water and freeze-dried overnight in vacuo to a give a yellow powder (98 mg, 28%) mp 165–168° C.: $R_F$ (petroleum ether:ethyl acetate:acetic acid 39:9:1) 0.50. $^1$H NMR (d6 DMSO) δ7.74 (s, 1H, C═C—H), 5.17 (s, 2H, OCH$_2$Ph), 4.74 (s, 2H, NCH$_2$Ph), 4.72 (s, 2H, C$\underline{H}_2$CO$_2$H).

EXAMPLE 41 alpha-Propyl 5-[[[3-(Dibenzylamino)carbonyl-4-(phenylmethoxy)]-phenyl]methylene]-4-oxo-2-thioxo-3-thiazolidineacetic acid

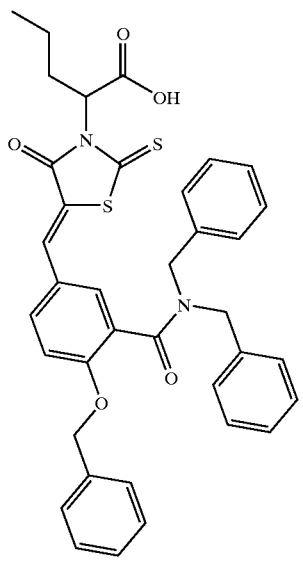

This compound was prepared from rhodanine-3-alpha-n-propylacetic acid (200 mg, 1 eq) and N,N-dibenzyl-2-benzyloxy-5-formylbenzamide (373 mg, 1 eq) using the same procedure as for Example 28, but the product did not precipitate from the reaction mixture. Instead, the reaction mixture was diluted with ethyl acetate (20 mL), and washed with water (2×20 mL). The organic solution was dried over sodium sulfate and evaporated in vacuo, and the residue was chromatographed on silica with ethyl acetate:petroleum ether:acetic acid (29:19:1) as eluent. This gave a gummy solid, which was recrystallized from acetone and petroleum ether, then suspended in water and freeze-dried overnight in vacuo to give the product as a yellow powder (32 mg, 6%): $^1$H NMR (CDCl$_3$) δ7.51 (s, 1H, C═C—H), 5.72 (m, 1H, C$\underline{H}$CO$_2$H), 5.34 (d, 1H, NCH$_2$Ph), 5.23 (d, 1H, OCH$_2$Ph), 5.15 (d, 1H, OCH$_2$Ph), 4.40 (d, 1H, NCH$_2$Ph), 4.10 (d, 1H, NCH$_2$Ph), 4.09 (d, 1H, NCH$_2$Ph), 2.25 (2H, m, C$\underline{H}_2$CH$_2$), 1.33 (m, 2H, CH$_2$C$\underline{H}_2$), 0.90 (t, 3H, CH$_3$).

EXAMPLE 42 alpha-Phenylmethyl 5-[[[3-(Dibenzylamino)carbonyl-4-(phenylmethoxy)]-phenyl]methylene]-4-oxo-2-thioxo-3-thiazolidineacetic acid

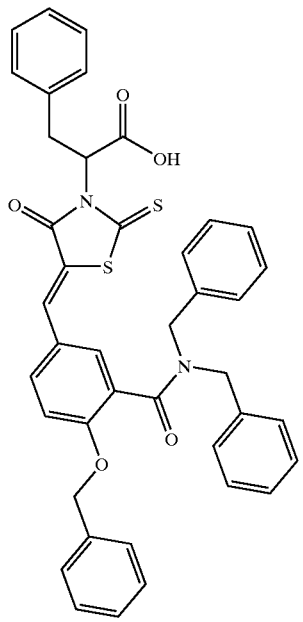

This compound was prepared from rhodanine-3-alpha-benzylacetic acid (200 mg, 1 eq) and N,N-dibenzyl-2-benzyloxy-5-formylbenzamide (309 mg, 1 eq) using the same procedure as for Example 28. The product precipitated from the reaction solution as a gummy solid, which was chromatographed on silica with petroleum ether:ethyl acetate:acetic acid (49:49:1) as eluent. This gave a yellow powder, which was suspended in water and freeze-dried overnight in vacuo (81 mg, 16%). mp 104–107° C. $^1$H NMR (CDCl$_3$) δ7.41 (s, 1H, C═C—H), 5.95 (broad s, 1H, C$\underline{H}$CO$_2$H), 5.33 (d, 1H, NCH$_2$Ph), 5.22 (d, 1H, OCH$_2$Ph), 5.15 (d, 1H, OCH$_2$Ph), 4.39 (d, 1H, NCH$_2$Ph), 4.15 (d, 1H, NCH$_2$Ph), 4.13 (d, 1H, NCH$_2$Ph), 3.57 (2H, d, CHC$\underline{H}_2$Ph).

EXAMPLE 43
(R)-5-[[[3-(N-α-(Acetoxymethyl)benzyl-N-benzylamino)carbonyl-4-(phenylmethoxy)]-phenyl]methylene]-4-oxo-2-thioxo-3-thiazolidineacetic acid

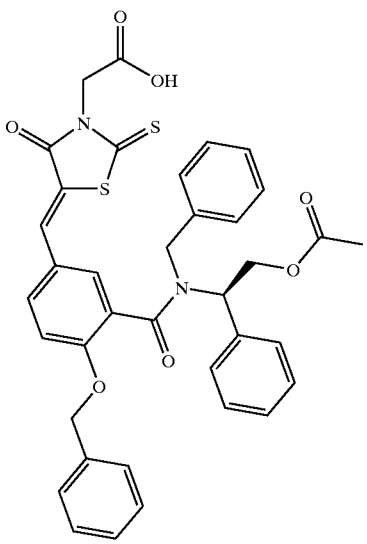

This compound was prepared from (R)-N-benzyl-N-α-(hydroxymethyl)benzyl-2-benzyloxy-5-formylbenzamide (140 mg, 1.2 eq) using the same procedure as for Example 40, except that after chromatography, the product was recrystallized from ethyl acetate/ether/petroleum ether and obtained as a yellow powder (29 mg, 17%) mp 146–148° C.: $^1$H NMR (d6 DMSO, 25° C., rotamers) δ1.96, 1.93, 1.89 and 1.57 (4×s, 3H, OCOCH$_3$); (d6 DMSO, 120° C.) 7.74 (s, 1H, C=CH), 5.26 (s, 2H, OCH$_2$Ph), 4.73 (s, 2H, CH$_2$CO$_2$H), 1.88 (s, 3H, OCOCH$_3$).

EXAMPLE 44
5-[[[3-(N,N-Dipentylamino)carbonyl-4-(2-phenylethoxy)]-phenyl]methylene]-4-oxo-2-thioxo-3-thiazolidineacetic acid

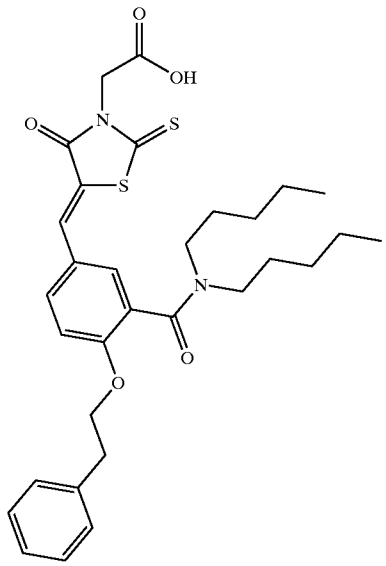

This compound was prepared from N,N-di-n-pentyl-2-(2-phenylethyl)oxy-5-formylbenzamide (400 mg, 0.98 mmol, 1 eq) using the same procedure as for Example 28, except that the product was washed with water instead of petroleum ether (300 mg, 53%) mp 181° C.: $^1$H NMR (d6 DMSO) δ7.89 (s, 1H, C=C—H), 7.70 (dd, 1H, J 8.7 and 2.2 Hz, ArH), 7.43 (d, 1H, J 2.2 Hz, ArH), 4.73 (s, 2H, CH$_2$CO$_2$H), 4.35 (t, 2H, J 5.9 Hz, OCH$_2$CH$_2$Ph), 3.58 (m, 1H, NCH$_2$), 3.15 (m, 1H, NCH$_2$), 3.01 (m, 2H, OCH$_2$CH$_2$Ph), 2.80 (m, 2H, NCH$_2$CH$_2$).

EXAMPLE 45
5-[[4-(2-Phenylethoxy)-3-[(N-phenyl-N-2-n-propyl-n-pentylcarbonyl)aminomethyl]-phenyl]methylene]-4-oxo-2-thioxo-3-thiazolidineacetic acid

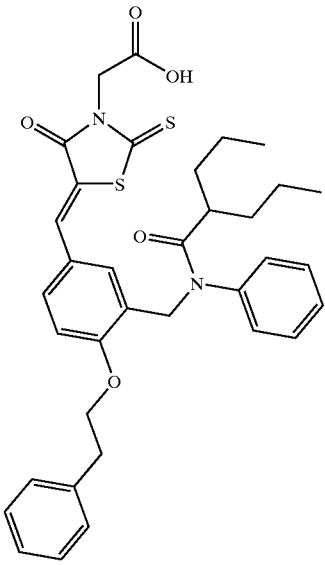

This compound was prepared from [N-phenyl-N-(2-(2-phenylethoxy)-5-formylbenzyl]-2-n-propyl-n-pentylamide (140 mg, 1 eq) using the procedure described in Example 28, except that the reaction required 48 h. During work-up the product began to crystallize from the organic layer, and petroleum ether was added to quicken this process. The resultant product was collected by filtration and washed with diethyl ether (57 mg, 29%) mp 232° C.: $^1$H NMR (d6 DMSO) δ7.80 (s, 1H, C=C—H), 7.60 (dd, 1H, J 8.7 and 2.1 Hz, ArH), 4.87 (s, 2H, CH$_2$N), 4.73 (s, 2H, CH$_2$CO$_2$H), 4.11 (t, 2H, J 6.4 Hz, OCH$_2$CH$_2$Ph), 2.85 (t, 2H, J 6.4 Hz, OCH$_2$CH$_2$Ph), 2.29 (m, 1H, COCH), 0.72 (t, 6H, J 7.2 Hz, 2×CH$_3$).

EXAMPLE 46

5-[[[3-(Dipentylamino)carbonyl-4-methoxy]phenyl]methylene]-4-oxo-2-thioxo-3-thiazolidineacetic acid

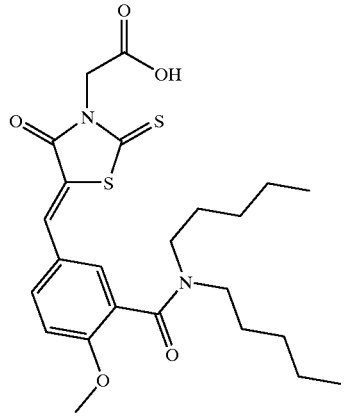

This compound was prepared from N,N-di-n-pentyl-2-methoxy-5-formylbenzamide (336 mg, 1 eq) using the same procedure as for Example 28 and was obtained as a yellow powder (278 mg, 54%). $^1$H NMR (d6 DMSO) δ7.87 (s, 1H, C═C—H), 4.69 (s, 2H, CH$_2$CO$_2$H), 3.94 (m, 1H, NCH$_2$), 3.86 (s, 3H, OCH$_3$), 3.51 (m, 1H, NCH$_2$), 3.29 (m, 1H, NCH$_2$), 2.99 (m, 1H, NCH$_2$).

EXAMPLE 47

5-[[[3-((S)-N-Benzyl-N-alpha-methylbenzylamino)carbonyl-4-methoxy]phenyl]methylene]-4-oxo-2-thioxo-3-thiazolidineacetic acid

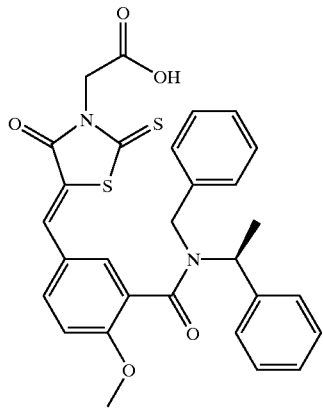

This compound was prepared from (S)-N-benzyl-N-alpha-methylbenzyl-2-methoxy-5-formylbenzamide (469 mg, 1.2 eq) using the same procedure as for Example 34 and was obtained as a yellow powder (330 mg, 58%) mp 175–179° C.: $^1$H NMR (d6 DMSO) (rotamers) δ8.03, 7.89 and 7.63 (3×s, 1H, C═C—H), 4.76 and 4.73 (2×s, 2H, CH$_2$CO$_2$H), 4.06 and 4.03 (2×s, 3H, OCH$_3$), 1.57, 1.54 and 1.41 (3×d, 3H, CHCH$_3$).

EXAMPLE 48

5-[[[3-(Dipentylamino)carbonyl-4-hydroxy]phenyl]methylene]-4-oxo-2-thioxo-3-thiazolidineacetic acid

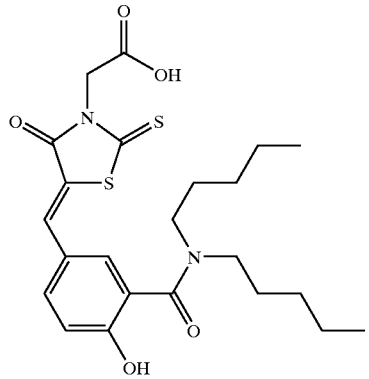

This compound was prepared from N,N-di-n-pentyl-2-hydroxy-5-formylbenzamide (211 mg, 1 eq) using the same procedure as for Example 28, but the product did not precipitate cleanly from the reaction mixture. The crude product was dissolved in saturated aqueous sodium bicarbonate (20 mL) and the aqueous solution washed with ethyl acetate (20 mL), then acidified to pH 1 with 10% HCl and back extracted with ethyl acetate (2×20 mL). The organic extracts were combined, washed with brine (20 mL), dried over sodium sulfate and evaporated in vacuo to give a yellow powder which was suspended in water and freeze-dried overnight in vacuo (69 mg, 21%) mp 188–192° C.: $^1$H NMR (CD$_3$OD) δ7.75 (s, 1H, C═C—H), 4.82 (s, 2H, CH$_2$CO$_2$H), 3.53 (m, 2H, NCH$_2$), 3.21 (m, 2H, NCH$_2$).

EXAMPLE 49

5-[[[3-(N,N-Dipentylamino)carbonyl-4-[(2,4-difluorophenyl)-methoxy]]phenyl]methylene]-4-oxo-2-thioxo-3-thiazolidineacetic acid

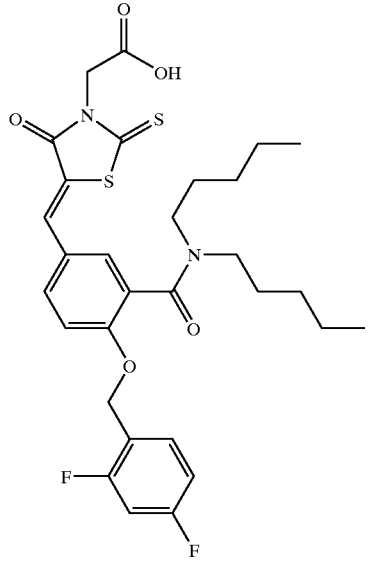

This compound was prepared from N,N-di-n-pentyl-2-(2,4-difluorobenzyl)oxy-5-formylbenzamide (226 mg, 1 eq) using the same procedure as for Example 28 and was obtained as a yellow powder (152 mg, 48%) mp 158–162° C.: $^1$H NMR (d6 DMSO) δ7.91 (s, 1H, C═C—H), 5.23 (s, 2H, CH$_2$Ar), 4.73 (s, 2H, CH$_2$CO$_2$H), 3.67 (m, 1H, NCH$_2$), 3.23 (m, 1H, NCH$_2$), 2.99 (m, 2H, NCH$_2$).

EXAMPLE 50

5-[[[3-(N,N-Dipentylamino)carbonyl-4-(trifluorophenyl)-methoxy]phenyl]methylene]-4-oxo-2-thioxo-3-thiazolidineacetic acid

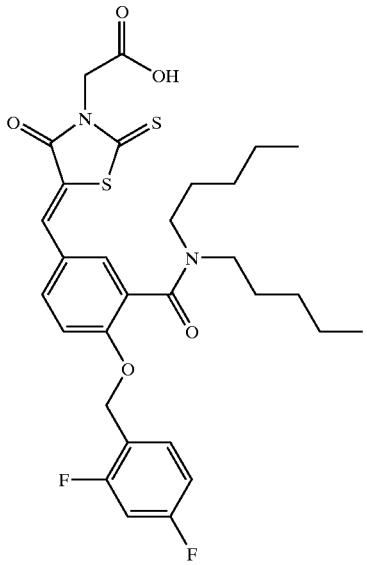

This compound was prepared from N,N-di-n-pentyl-2-(4-trifluoromethylbenzyl)oxy-5-formylbenzamide (242 mg, 1 eq) using the same procedure as for Example 28 and was obtained as a yellow powder (267 mg, 80%) mp 164–168° C.: $^1$H NMR (d6 DMSO) δ7.90 (s, 1H, C=C—H), 5.34 (s, 2H, CH$_2$Ar), 4.70 (s, 2H, C$\underline{H}_2$CO$_2$H), 3.69 (m, 1H, NCH$_2$), 3.18 (m, 1H, NCH$_2$), 3.03 (m, 2H, NCH$_2$).

EXAMPLE 51

5-[[[4-(Dibenzylamino)carbonyl-3-(phenylmethoxy)]-phenyl]methylene]-4-oxo-2-thioxo-3-thiazolidineacetic acid

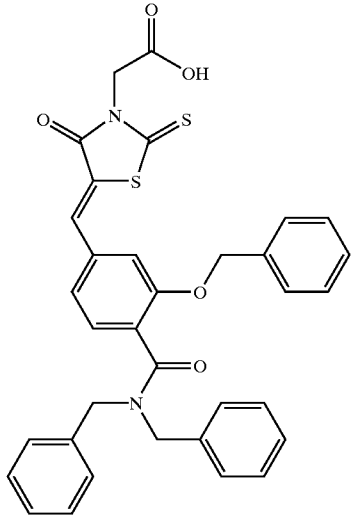

This compound was prepared from N,N-dibenzyl-2-benzyloxy-4-formylbenzamide (236 mg, 1.2 eq) using the same procedure as for Example 34 Chromatography of the crude product on silica, with petroleum ether:ethyl acetate:acetic acid (32:16:1) as eluent, gave a gummy solid which was recrystallized from a mixture of ethyl acetate, diethyl ether and petroleum ether. The product, a yellow powder, was suspended in water and freeze-dried overnight in vacuo (140 mg, 51%) mp 109–113° C.: $^1$H NMR (d6 DMSO) δ7.90 (s, 1H, O=C—H), 5.30 (s, 2H, OCH$_2$Ph), 5.11 (d, 1H, NCH$_2$Ph), 4.74 (s, 2H, C$\underline{H}_2$CO$_2$H), 4.41 (d, 1H, NCH$_2$Ph), 4.13 (d, 1H, NCH$_2$Ph), 4.01 (d, 1H, NCH$_2$Ph).

EXAMPLE 52

5-[[3-[(Dipentylamino)methyl]-4-(phenylmethoxy)phenyl]methylene]-4-oxo-2-thioxo-3-thiazolidineacetic acid

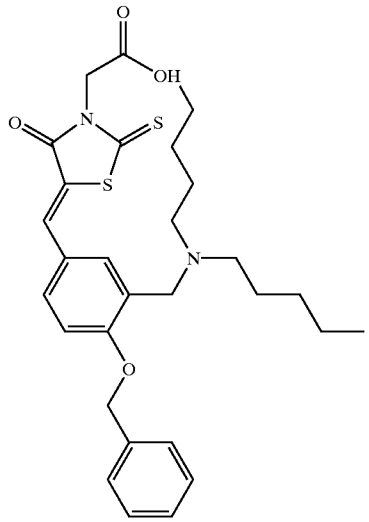

This compound was prepared from 3-[(dipentylamino)methyl]-4-phenylmethoxy-benzaldehyde (165 mg, 1 eq) using the same procedure as for Example 28. As no solid precipitate formed from the reaction mixture, it was partitioned between water and ethyl acetate. An emulsion formed which was dispersed by the addition of brine. A gum started to form which was redissolved by addition of methanol. The organic layer was passed over some sodium sulfate and evaporated under reduced pressure to give a residue which was redissolved in a mixture of ethyl acetate and methanol. Addition of diethyl ether to the solution gave a precipitate which was filtered, washed with diethyl ether, then dried in vacuo to give a yellow powder, 5-[[4-phenylmethoxy-3-[(dipentylamino)methyl]phenyl]methylene]-4-oxo-2-thioxo-3-thiazolidineacetic acid, (165 mg). $^1$H NMR (d6 DMSO) δ7.83 (s, 1H, C=C—H); 5.25 (s, 2H, C$\underline{H}_2$Ph); 4.68 (s, 2H, C$\underline{H}_2$CO$_2$H); 4.07 (m, 2H); 2.75 (m, 4H); 1.57 (m, 4H); 1.19 (m, 8H); 0.81 (t, 6H).

EXAMPLE 53

5-[[4-Phenylmethoxy-3-[[N-phenylmethyl-N-(2-phenylethyl)amino]-methyl]phenyl]methylene]-4-oxo-2-thioxo-3-thiazolidineacetic acid

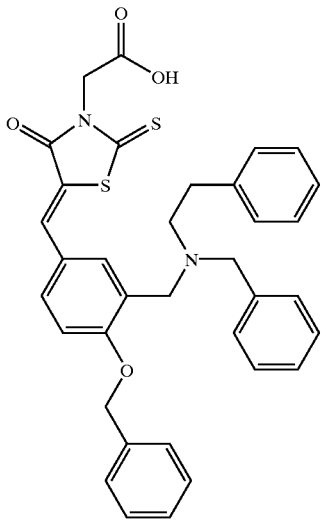

This compound was prepared from 4-phenylmethoxy-3-[[N-phenylmethyl-N-(2-phenylethyl)amino]methyl]benzaldehyde (143 mg, 1 eq) using the same procedure as for Example 28. As no solid precipitated formed from the reaction mixture it was partitioned between water and ethyl acetate. The organic layer was dried over sodium sulfate, partially evaporated under reduced pressure. The concentrate was treated with diethyl ether and petroleum ether to give a yellow precipitate, 5-[[4-phenylmethoxy-3-[[N-phenylmethyl-N-(2-phenylethyl)amino]methyl]phenyl]-methylene]-4-oxo-2-thioxo-3-thiazolidine-acetic acid, (57 mg). $^1$H NMR (d6 DMSO) δ7.74 (s, 1H, C=C—H); 5.21 (s, 2H, CH$_2$Ph); 4.75 (s, 2H, C$\underline{H}_2$CO$_2$H); 3.73 (s, 2H, NCH$_2$); 3.65 (s, 2H, NCH$_2$); 2.80 (m, 2H, C$\underline{H}_2$CH$_2$); 2.65 (m, 2H, CH$_2$C$\underline{H}_2$).

EXAMPLE 54

5-[[3-[(Dibenzylamino)methyl]-4-(phenylmethoxy)phenyl]methylene]-4-oxo-2-thioxo-3-thiazolidineacetic acid

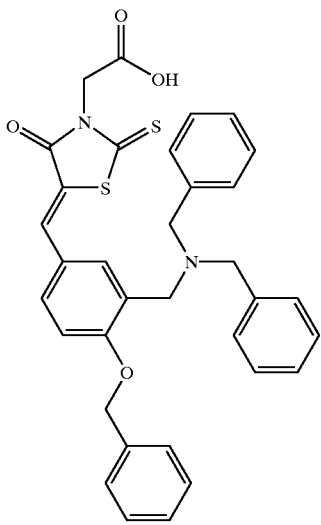

This compound was prepared from 3-[(dibenzylamino)methyl]-4-phenylmethoxy-benzaldehyde (129 mg, 1 eq) using the same procedure as for Example 28. As no solid precipitated formed from the reaction mixture it was partitioned between water and diethyl ether. The organic layer was evaporated under reduced pressure, the residue dissolved in ethyl acetate and petroleum ether added to give a yellow precipitate, 5-[[3-[(dibenzylamino)methyl]-4-(phenylmethoxy)phenyl]methylene]-4-oxo-2-thioxo-3-thiazolidineacetic acid, (140 mg). $^1$H NMR (d6 DMSO) δ7.82 (m, 2H, C=C—H and ArH); 5.20 (s, 2H, CH$_2$Ph); 4.70 (s, 2H, C$\underline{H}_2$CO$_2$H); 3.56 (m, 6H, NCH$_2$).

EXAMPLE 55

5-[[4-Phenylmethoxy-3-[[(4-phenyl)-1-piperazinyl]methyl]phenyl]-methylene]-4-oxo-2-thioxo-3-thiazolidineacetic acid

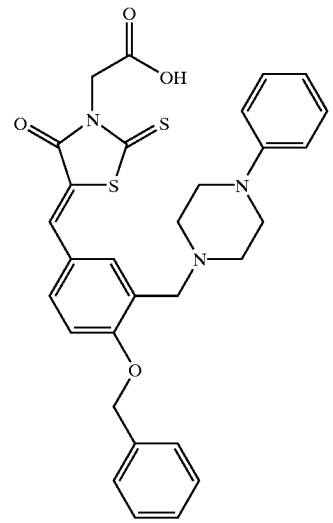

This compound was prepared from 4-phenylmethoxy-3-[(4-phenyl)-1-piperazinyl]methyl]benzaldehyde (110 mg, 1 eq) using the same procedure as for Example 28. As no solid precipitate formed from the reaction mixture it was diluted with twice its volume of water (which gave an emulsion) and put on to a short column of HP20SS resin (pH stable reverse phase) and eluted successively with 33% aqueous acetic acid, 75% and finally 100% acetic acid. The 75% and 100% fractions were evaporated under reduced pressure to give a yellow powder, 5-[[4-phenylmethoxy-3-[[(4-phenyl)-1-piperazinyl]methyl]phenyl]-methylene]-4-oxo-2-thioxo-3-thiazolidine acetic acid, (148 mg). $^1$H NMR (d6 DMSO) δ7.85 (s, 1H, C=C—H); 5.30 (s, 2H, CH$_2$Ph); 4.68 (s, 2H, C$\underline{H}_2$CO$_2$H); 3.68 (s, 2H, CH$_2$N); 3.20 (s, 4H, NC$\underline{H}_2$CH$_2$N); 2.60 (s, 4H, NCH$_2$C$\underline{H}_2$N).

EXAMPLE 56

5-[[3-[N-ethyl-N-(2-phenylethyl)amino]methyl-4-(phenylmethoxy)-phenyl]methylene]-4-oxo-2-thioxo-3-thiazolidineacetic acid

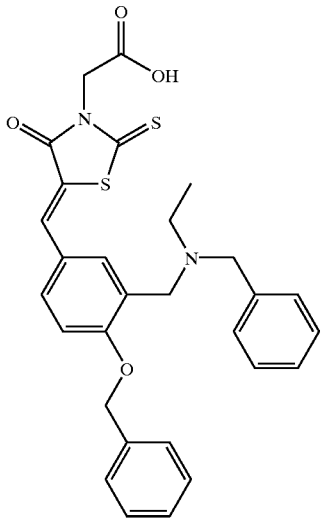

This compound was prepared from 4-benzyloxy-3-[[[N-(phenylmethyl)-N-ethyl]amino]methyl]benzaldehyde (164 mg, 1 eq) using the same procedure as for Example 28. As no solid precipitated formed from the reaction mixture it was partitioned between water and ethyl acetate. The organic layer was dried over sodium sulfate and partially evaporated under reduced pressure. Diethyl ether and petroleum ether were then added to give a yellow precipitate, 5-[[3-[N-ethyl-N-(2-phenylethyl)amino]methyl-4-(phenylmethoxy)phenyl]methylene]-4-oxo-2-thioxo-3-thiazolidineacetic acid, (67 mg). $^1$H NMR (d6 DMSO) δ7.86 (s, 1H, C=C—H); 5.23 (s, 2H, CH$_2$Ph); 4.73 (s, 2H, C$\underline{H}_2$CO$_2$H); 3.69 (s, 2H, NCH$_2$); 3.64 (s, 2H, NCH$_2$); 2.50 (m, 2H, C$\underline{H}_2$CH$_3$); 1.06 (t, 3H, CH$_2$C$\underline{H}_3$).

EXAMPLE 57

5-[[4-Phenylmethoxy-3-[[(4-phenylmethyl)-1-piperidinyl]methyl]-phenyl]methylene]-4-oxo-2-thioxo-3-thiazolidineacetic acid

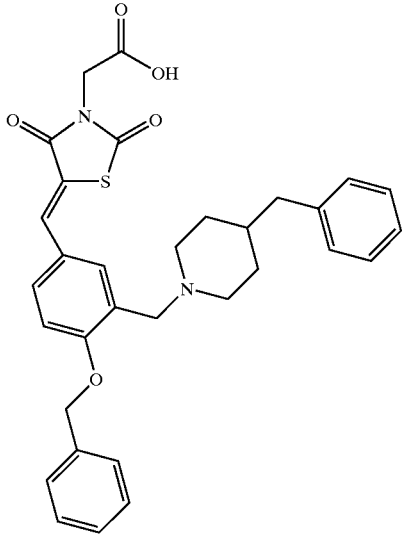

This compound was prepared from 4-phenylmethoxy-3-[[4-(phenylmethyl)-1-piperidinyl]methyl]benzaldehyde (110 mg, 1 eq) using the same procedure as for Example 28. As no solid precipitated formed from the reaction mixture it was diluted with water and put on to a short column of HP20SS resin (pH stable reverse phase) and eluted with 50% aqueous acetic acid and then 100% acetic acid. The 100% fractions were evaporated under reduced pressure to give an orange powder, 5-[[4-phenylmethoxy-3-[[(4-phenylmethyl)-1-piperidinyl]methyl]-phenyl]methylene]-4-oxo-2-thioxo-3-thiazolidineacetic acid, (105 mg). $^1$H NMR (d6 DMSO) δ7.83 (s, 1H, C=C—H); 5.20 (s, 2H, CH$_2$Ph); 4.60 (s, 2H, CH$_2$CO$_2$H); 3.80 (s, 2H, C$\underline{H}_2$N).

Biological Assays

Example 1

PMT-1 Assay

The assay method is based upon the transfer of a radio-labelled mannose moiety from dolicholphosphomannose onto a threonine hydroxyl residue in a short peptide, as catalysed by the *Candida albicans* PMT-1 enzyme. Dolicholphospho-[$^3$H]-mannose is synthesised enzymatically from GDP-[$^3$H]-mannose and purified by chloroform:methanol extraction.

100000 Dpm of the generated substrate is incubated with 400 μg phosphatidylcholine, 25 μg of peptide (DYATAV) and 25 μg of *Candida albicans* membrane protein in a final volume of 50 μl in 100 mM Tris/1 mM MgCl$_2$ buffer, pH 8.0. After 60 minutes at 25° C., the reaction is stopped with 50 μl of methanol. The unreacted radiolabel is removed by the addition of 150 μl of 0.4 g/ml octadecyl-functionalised silica (C18) in methanol. The C18 material is removed by centrifugation and the activity transferred to the peptide is counted in the supernatant.

Example 2

G418 Sensitivity Assay

This assay is based upon the observed increased sensitivity of the pmt1−/− Candida strain to Geneticin (G418) (6). 100 μl of a 0.1OD$_{600\ nm}$ culture of *Candida albicans* (strain SC5314) is placed into a 96 well plate in the presence or absence of varying concentrations of test compound. The compounds are initially dissolved in DMSO and added to the cultures at a final DMSO concentration of 1%. G418 is added to a final concentration of 100 μg/ml. In the absence of PMT1 inhibition, this concentration of G418 has no effect on the proliferation of the organism. The cultures are grown overnight at 37° C. and cell density is then estimated by an OD$_{600\ nm}$ measurement. The effect of the test compound is calculated as the concentration that gives a 50% reduction in cell growth relative to the culture with G418 alone.

|  | PMT-1 Inhibition (IC$_{50}$, μM) | G418 Sensitivity (IC$_{50}$, μM) |
| --- | --- | --- |
| Example 34 | 2.5 | 1.5 |
| Example 35 | 0.6 | 0.65 |
| Example 49 | 0.7 | 0.7 |

What is claimed is:
1. A compound of Formula I or a salt or prodrug thereof

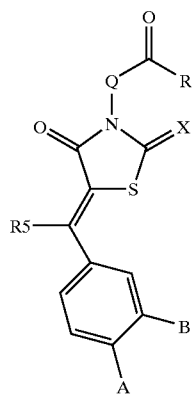

Formula I wherein X is O or S;
A and B are OR2 or Y—NR3R4, wherein when A is OR2, B is Y—NR3R4 and vice versa, or when one of A or B is OR2, then the other can be $CO_2R7$;
Y is $CH_2$ or C=O;
Q is $(CH_2)_m$—CH(R1)—$(CH_2)_n$;
R is OR6 or NHR7;
R1 is hydrogen, $C_1$–$C_6$ branched or straight chain alkyl optionally substituted with hydroxyl, $C_1$–$C_3$ alkylphenyl or phenyl;
R2 is hydrogen, $C_1$–$C_{10}$ branched or straight chain alkyl, $C_3$–$C_{10}$ cycloalkyl, $C_2$–$C_{10}$ branched or straight chain alkenyl, $C_2$–$C_{10}$ branched or straight chain alkynyl, $(CH_2)_m$—$(CF_2)_n CF_3$, $(CH_2)_n CH(R10)$—$(CH_2)_q$-aryl or $(CH_2)_p$-aryl, where aryl is phenyl, pyridyl, thienyl or furyl; wherein phenyl is optionally substituted by one or more substituents sciected from F, Cl, Br, $CF_3$, $OCF_3$, OR6, $C_1$–$C_6$ branched or straight chain alkyl, COR, CN, $SO_2R9$, or $SONR7R8$, and pyridyl, thienyl or furyl are optionally substituted by F, Cl, Br, $CF_3$, OR6 or $C_1$–$C_6$ branched or straight chain alkyl;
R3 and R4 are independently hydrogen, $C_1$–$C_6$ branched or straight chain alkyl, C(=O)R6, —CH$(CH_2OCOR8)$-aryl or CH(R8)—$(CH_2)_p$-aryl where aryl is phenyl, pyridyl, thienyl or fury; wherein phenyl is optionally substituted by one or more substituents selected from F, Cl, Br, $CF_3$, $OCF_3$, OR6, $C_1$–$C_6$ branched or straight chain alkyl, COR, CN, $SO_2R7$ or phenyl;
or R3 and R4 when taken together may form a 4–7 membered ring optionally incorporating an additional heteroatom, selected from O, N or S, wherein the ring may be optionally substituted at any position with $(CH_2)_p$-aryl where aryl is phenyl optionally substituted by one or more substituents selected from F, Cl, Br, $CF_3$, $OCF_3$, $C_1$–$C_6$ branched or straight chain alkyl, COR, CN, $SO_2R8$ or phenyl;
R5 is hydrogen;
R6 and R7 are independently hydrogen, $C_1$–$C_{10}$ branched or straight chain alkyl or $(CH_2)_p$-phenyl;
R8 is hydrogen or $C_1$–$C_3$ alkyl;
R9 is $C_1$–$C_6$ branched or straight chain alkyl or phenyl;

R10 is hydrogen, $C_1$–$C_{10}$ branched or straight chain alkyl, $(CH_2)_p$-aryl where aryl is phenyl optionally substituted by one or more substituents selected from F, Cl, Br, $CF_3$, $OCF_3$, $C_1$–$C_6$ branched or straight chain alkyl, COR, CN, $SO_2R8$;
and m, n and p are integers wherein m is 0–3; n is 0–2; and p is 0–3.

2. A compound as claimed in claim 1 in which:
X is O or S;
A and B are OR2 or Y—NR3R4 wherein when A is OR2, B is Y—NR3R4, and vice versa,
or when one of A or B is OR2, then the other can be $CO_2R7$;
Y is $CH_2$ or C=O;
Q is CH(R1);
R is OH;
R1 is hydrogen, $C_1$–$C_6$ alkyl or $C_1$–$C_3$ alkylphenyl;
R2 is hydrogen, $C_1$–$C_{10}$ branched or straight chain alkyl, $(CH_2)_p$-phenyl, wherein phenyl is optionally substituted by one or more substituents selected from F and $CF_3$;
R3 and R4 are independently hydrogen, $C_1$–$C_6$ branched or straight chain alkyl, $(CH_2)_p$-phenyl, C(=O)$C_1$–$C_{10}$ branched or straight chain alkyl, —CH(R8)-phenyl, CH$(CH_2OCOR8)$-phenyl, or R3 and R4 together foini a morpholino, piperidinyl or piperazinyl group optionally substituted with $(CH_2)_p$-phenyl;
R5 is hydrogen;
and p is an integer from 0–3.

3. A compound as claimed in claim 1 which is:
5-[[[3-(N-Methyl-N-phenylamino)carbonyl-4-(phenylmethoxy)]-phenyl]methylene]-4-oxo-2-thioxo-3-thiazolidineacetic acid;
5-[[[3-(N,N-Dibenzylamino)carbonyl-4-(phenylmethoxyl)]-phenyl]methylene]-4-oxo-2-thioxo-3-thiazolidincacetic acid;
5-[[[3-(N,N-Dipentylamino)carbonyl-4-(phenylmethoxyl)]-phenyl]methylene]-4-oxo-2-thioxo-3-thiazolidineacetic acid;
5-[[[3-((S)-N-Benzyl-N-alpha-methylbenzylamino)carbonyl-4-(phenylmethoxyl)]-phenyl]methylene]-4-oxo-2-thioxo-3-thiazolidineacetic acid;
5-[[[3-(N,N-Dibutylamino)carbonyl-4-(phenylmethoxyl)]-phenyl]methylene]-4-oxo-2-thioxo-3-thiazolidineacetic acid;
5-[[[3-(N-Benzyl-N-butylamino)carbonyl-4-(phenylmethoxy)]-phenyl]methylene]-4-oxo-2-thioxo-3-thiazolidineacctic acid;
5-[[[3-((R)-N-alpha-methylbenzylamino)carbonyl-4-(phenylmethoxy)]-phenyl]methylene]-4-oxo-2-thioxo-3-thiazolidineacetic acid;
5-[[[3-((S )-N-methyl-N-alpha-methylbenzylamino)carbonyl-4-(phenylmethoxy)]-phenyl]methylene]-4-oxo-2-thioxo-3-thiaolidineacetic acid;
5-[[[3-(Dipentylamino)carbonyl-4-methoxy]phenyl]methylene]-4-oxo-2-thioxo-3-thiazolidineacetic acid;
5-[[[3-((S)-N-Benzyl-N-alpha-methylbenzylamino)carbonyl-4-methoxy]-phenyl]methylene]-4-oxo-2-thioxo-3-thiazolidineacetic acid;
5-[[[3-(N,N-Dipentylamino)carbonyl-4-[(2,4-difluorophenyl)-methoxyl]phenyl]methylene]-4-oxo-2-thioxo-3-thiazolidineacetic acid;

5-[[[3-(N,N-Dipentylamino)carhonyl-4-(trifluorophenyl)-methoxy]phenyl]methylene]-4-oxo-2-thioxo-3-thiazolidineacetic acid;

5-[[3-[(Dibenzylamino)methyl]-4-phenylmethoxy)phenyl]methylene]-4-oxo-2-thioxo-3-thiazolidineacetic acid;

5-[[3-[(Dipentylamino)methyl]-4-(phenylmethoxy)phenyl]methylene]-4-oxo-2-thioxo--3-thiazolidineacetic acid;

(R)-5-[[[3-(N-α-(Acetoxymethyl)benzyl-N-benzylamino)carbonyl-4-(phenylmethoxy)]-phenyl]methylene]-4-oxo-2-thioxo-34-thiazolidineacetic acid;

5-[[[3-(N,N-Dipentylamino)carhonyl-4-(2-phenylethoxy)]-phenyl]methylene]-4-oxo-2-thioxo-3-thiazolidincacetic acid; or 5-[[4-(2-Phenylethoxy)-3-[(N-phenyl-N-2-n-propyl-n-petylcarbonyl)aminomethyl]-phenyl]methylene]-4-oxo-2-thioxo-3-thiazolidincaetic acid.

4. A pharmaceutical composition comprising at least one compound as claimed in claim 1 and one or more pharmaceutically acceptable carriers, excipients and/or diluents.

5. A method for the preparation of a compound as claimed in claim 1 comprising condensing a rhodanine-3-acetic acid of Formula (A)

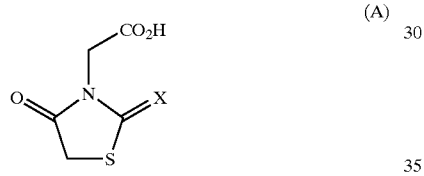

(A)

or an analogue or derivative thereof wherein X is O or S, with a substituted benzaldehyde derivative, ArCHO, wherein Ar corresponds to a group having the structure

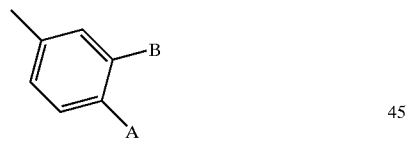

under general acid-base catalysis conditions with the application of heat.

Scheme 1

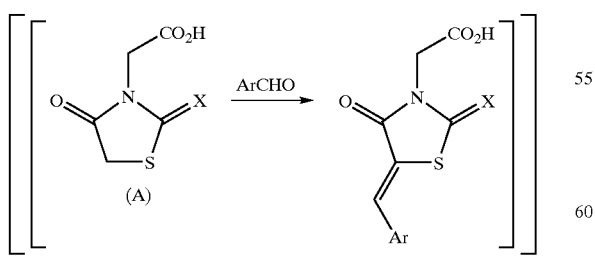

6. A method for the prophylaxis or treatment of an individual suffering from a fungal infection comprising administering to the individual a compound of Formula I or a salt or prodrug thereof

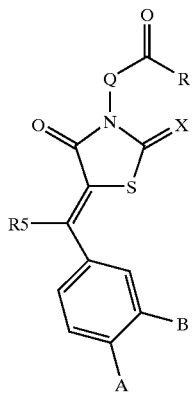

Formula I wherein X is O or S;

A and B are OR2 or Y—NR3R4, wherein when A is OR2, B is Y—NR3R4 and vice versa, or when one of A or B is OR2, then the other can be $CO_2R7$;

Y is $CH_2$ or C=O;

Q is $(CH_2)_m$—CH(R1)—$(CH_2)_n$;

R is OR6 or NHR7;

R1 is hydrogen, $C_1$–$C_6$ branched or straight chain alkyl optionally substituted with hydroxyl, $C_1$–$C_3$ alkylphenyl or phenyl;

R2 is hydrogen, $C_1$–$C_{10}$ branched or straight chain alkyl, $C_3$–$C_{10}$ cycloalkyl, $C_2$–$C_{10}$ branched or straight chain alkenyl, $C_2$–$C_{10}$ branched or straight chain alkynyl, $(CH_2)_m$—$(CF_2)_n CF_3$, $(CH_2)_n$—CH(R10)—$(CH_2)_q$-aryl or $(CH_2)_p$-aryl, where aryl is phenyl, pyridyl, thienyl or furyl; wherein phenyl is optionally substituted by one or more substituents selected from F, Cl, Br, $CF_3$, $OCF_3$, OR6, $C_1$–$C_6$ branched or straight chain alkyl, COR, CN, $SO_2R9$, or $SONR7R8$, and pyridyl, thienyl or furyl are optionally substituted by F, Cl, Br, $CF_3$, OR6 or $C_1$–$C_6$ branched or straight chain alkyl;

R3 and R4 are independently hydrogen, $C_1$–$C_6$ branched or straight chain alkyl, C(=O)R6, —CH($CH_2OCOR8$)-aryl or CH(R8)—$(CH_2)_p$-aryl where aryl is phenyl, pyridyl, thienyl or furyl; wherein phenyl is optionally substituted by one or more substituents selected from F, Cl, Br, $CF_3$, $OCF_3$, OR6, $C_1$–$C_6$ branched or straight chain alkyl, COR, CN, $SO_2R7$ or phenyl;

or R3 and R4 when taken together may form a 4–7 membered ring optionally incorporating an additional heteroatom, selected from O, N or S, wherein the ring may be optionally substituted at any position with $(CH_2)_p$-aryl where aryl is phenyl optionally substituted by one or more substituents selected from F, Cl, Br, $CF_3$, $OCF_3$, $C_1$–$C_6$ branched or straight chain alkyl, COR, CN, $SO_2R8$ or phenyl;

R5 is hydrogen, $C_1$–$C_6$ branched or straight chain alkyl or phenyl optionally substituted by one or more substituents selected from F, Cl, $Br_3$, $OCF_3$, OR6, $C_1$–$C_6$ branched or straight chain alkyl, COR, CN or $SO_2R9$;

R6 and R7 are independently hydrogen or $C_1$–$C_{10}$ branched or straight chain alkyl or $(CH_2)_p$-phenyl;

R8 is hydrogen or $C_1$–$C_3$ alkyl;

R9 is $C_1$–$C_6$ branched or straight chain alkyl or phenyl;

R10 is hydrogen, $C_1$–$C_{10}$ branched or straight chain alkyl, $(CH_2)_p$-aryl where aryl is phenyl optionally substituted by one or more substituents selected from F, Cl, Br, CF₃, OCF₃, C₁–C₆ branched or straight chain alkyl, COR, CN, SO₂R8;

and m, n and p are integers wherein m is 0–3; n is 0–2; and p is 0–3.

7. A method as claimed in claim 6 wherein the fungal infection is a Candida, Trichophyton, Microsporum, *Cryptococcus neoformans, Aspergillus flavus, Aspergillus fumigatus*, Coccidioides, Paracoccidioides, Histoplasma, Blastomyces or Epidermophyton infection.

8. The method according to claim 5 wherein the acid-base catalysis conditions comprise using sodium acetate in acetic acid or ammonium acetate in toluene, at the reflux temperature of the solvent.

9. A compound as claimed in claim 1 which is:

5-[[[3-(Phenylmethoxy)carbonyl-4-(phenylmethoxy)] phenyl]methylene]-4-oxo-2-thioxo-3-thiazolidineacetic acid;

5-[[[3-(N-Morpholinyl)carbonyl-4-(phenylmethoxy)] phenyl]methylene]-4-oxo-2-thioxo-3-thiazolidineacetic acid;

5-[[[3-(4-Phenyl-1-piperazinyl)carbonyl-4-(phenylmethoxy)]phenyl]methylene]-4-oxo-2-thioxo-3-thiazolidineacetic acid;

5-[[[3-(4-Benzyl-1-piperidinyl)carbonyl-4-(phenylmethoxy)]phenyl]methylene]-4-oxo-2-thioxo-3-thiazolidincacetic acid;

5-[[[3-(N-Benzyl-N-phenylamino)carbonyl-4-(phenylmethoxy)]phenyl]methylene]-4-oxo-2-thioxo-3-thiazolidineacetic acid;

alpha-Propyl 5-[[[3-(dibenzylamino)carbonyl-4-(phenylmethoxy)]phenyl]methylene]-4-oxo-2-thioxo-3-thiazolidineacetic acid;

alpha-Phenylmethyl 5-[[[3-(dibenzylamino)carbonyl-4 (phenylmethoxy)]phenyl]methylene]-4-oxo-2-thioxo-3-thiazolidineacetic acid;

5-[[[3-(Dipenlylamino)carbonyl-4-hydroxy]phenyl] methylene]-4-oxo-2-thioxo-3-thiazolidineacctic acid;

5-[[[4-(Dibenzylamino)carbonyl-3-(phenylmethoxy)] phenyl]methylene]-4-oxo-2-thioxo-3-thiazolidincacetic acid;

5-[[4-Phenylmethoxy-3-[[N-phenylmethyl-N-(2-phenylethyl)amino]methyl]phenyl]-methylene]-4-oxo-2-thioxo-3-thiazolidineacetic acid;

5-[[4-Phenylmethoxy-3-[[(4-phenyl)-1-piperazinyl] methyl]phenyl]methylene]-4-oxo-2-thioxo-3-thiazolidineacctic acid;

5-[[3-[N-Ethyl-N-(2-phenylethyl)amino]methyl-4-(phenylmethoxy)phenyl]-4-oxo-2-thioxo-3-thiazolidineacetic acid; or 5-[[4-Phenylmethoxy-3-[[(4-phenlylmethyl)-1-piperidinyl]methyl]phenyl]methylene]-4-oxo-2-thioxo-3-thiazol,dineacctic acid.

\* \* \* \* \*